(12) United States Patent
Huwais

(10) Patent No.: US 12,220,297 B2
(45) Date of Patent: Feb. 11, 2025

(54) AUTOGRAFTING TOOL FOR DEEP REACH APPLICATIONS

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 758 days.

(21) Appl. No.: 17/285,011

(22) PCT Filed: Nov. 6, 2019

(86) PCT No.: PCT/US2019/059964
§ 371 (c)(1),
(2) Date: Apr. 13, 2021

(87) PCT Pub. No.: WO2020/097144
PCT Pub. Date: May 14, 2020

(65) Prior Publication Data
US 2021/0290346 A1 Sep. 23, 2021

Related U.S. Application Data

(60) Provisional application No. 62/756,406, filed on Nov. 6, 2018.

(51) Int. Cl.
*A61C 8/00* (2006.01)
(52) U.S. Cl.
CPC .......... *A61C 8/0089* (2013.01); *A61C 8/0034* (2013.01)
(58) Field of Classification Search
CPC .......... A61C 8/0089; A61C 3/02; A61C 1/08; A61B 2017/1651; A61B 2017/1653; A61B 2217/007

(Continued)

(56) References Cited

U.S. PATENT DOCUMENTS

| 811,111 A | 1/1906 | Wegefarth |
| 2,113,178 A | 4/1938 | Gase |

(Continued)

FOREIGN PATENT DOCUMENTS

| CA | 2590344 C | 10/2017 |
| CN | 2232727 | 8/1996 |

(Continued)

OTHER PUBLICATIONS

WO 2018040917 Text translation (Year: 2018).*

(Continued)

*Primary Examiner* — Heidi M Eide
(74) *Attorney, Agent, or Firm* — Endurance Law Group PLC

(57) ABSTRACT

A rotary osteotome for deep reach applications. The body of the osteotome has a tapered end that supports helically spiraling flutes. Substantially margin-less (without margin) working edges are interleaved between the flutes to provide compaction action when rotated in a non cutting direction. The body also has an elongated cylindrical stopper section. An irrigation conduit passes through the center of the stopper section and emerges at a plurality of outlet orifices that function as independent nozzles for irrigating fluid. The outlet orifices are generally elliptical in shape and spaced around the body to maintain balance. The irrigation conduit has a main trunk that opens to a flow splitter, which in turn divides the flow of irrigating fluid into substantially equal branches. Each branch is angled at an acute trajectory relative to the longitudinal axis, in the direction of said apical end, between about 10° and 45°.

13 Claims, 14 Drawing Sheets

(58) Field of Classification Search
USPC .......................................................... 433/165
See application file for complete search history.

(56) References Cited

U.S. PATENT DOCUMENTS

| | | | |
|---|---|---|---|
| 2,489,179 | A | 11/1949 | Hartman |
| 3,239,275 | A | 3/1966 | Belugou |
| 3,556,669 | A | 1/1971 | Valeska et al. |
| D269,040 | S | 5/1983 | Deemer |
| 4,474,556 | A | 10/1984 | Ellis et al. |
| 4,850,867 | A | 7/1989 | Senia et al. |
| 5,220,964 | A | 6/1993 | Deken et al. |
| 5,261,818 | A * | 11/1993 | Shaw ...................... A61C 3/02 |
| | | | 433/165 |
| 5,377,773 | A | 1/1995 | Tibbitts |
| 5,443,468 | A | 8/1995 | Johnson |
| 5,489,179 | A | 2/1996 | Gabriel et al. |
| 5,536,127 | A | 7/1996 | Pennig |
| 5,667,509 | A | 9/1997 | Westin |
| 5,688,120 | A | 11/1997 | Yacker et al. |
| 5,702,443 | A | 12/1997 | Brånemark |
| 5,735,689 | A | 4/1998 | McSpadden |
| 5,762,498 | A | 6/1998 | Gonzalez |
| 5,839,897 | A | 11/1998 | Bordes |
| 5,891,146 | A | 4/1999 | Simon et al. |
| 6,146,138 | A | 11/2000 | Dalmau |
| 6,179,616 | B1 | 1/2001 | Danger |
| 6,186,787 | B1 | 2/2001 | Danger et al. |
| 6,264,677 | B1 | 7/2001 | Simon et al. |
| 6,561,805 | B2 | 5/2003 | Kumar |
| 6,641,395 | B2 | 11/2003 | Kumar et al. |
| 6,899,715 | B1 | 5/2005 | Beaty |
| 7,198,488 | B2 | 4/2007 | Lang et al. |
| 7,241,144 | B2 | 7/2007 | Nilo et al. |
| 7,247,020 | B2 | 7/2007 | Takahashi et al. |
| 7,300,281 | B2 | 11/2007 | Cantatore et al. |
| 7,402,040 | B2 | 7/2008 | Turri |
| 7,435,086 | B2 | 10/2008 | Berutti et al. |
| 7,488,327 | B2 | 2/2009 | Rathbun et al. |
| 7,547,210 | B1 | 6/2009 | Valen |
| D611,511 | S | 3/2010 | Aldecoa |
| 7,766,657 | B2 | 8/2010 | Jaunberzins |
| 8,070,398 | B2 | 12/2011 | Durfee |
| 8,080,012 | B2 * | 12/2011 | Chen ...................... A61C 8/0089 |
| | | | 606/86 R |
| 8,945,193 | B2 * | 2/2015 | Kirschman ........ A61B 17/8841 |
| | | | 606/317 |
| D736,928 | S * | 8/2015 | Iijima ........................... D24/152 |
| 9,211,137 | B2 * | 12/2015 | Voic ............... A61B 17/320068 |
| 9,271,740 | B2 | 3/2016 | Scianamblo |
| 9,326,778 | B2 | 5/2016 | Huwais |
| 10,006,253 | B2 | 6/2018 | DiGiovanni et al. |
| 10,039,621 | B2 * | 8/2018 | Huwais ................ A61C 8/0089 |
| 10,040,136 | B2 | 8/2018 | Shpigelman |
| 10,661,357 | B2 | 5/2020 | Chien et al. |
| 10,912,595 | B2 | 2/2021 | Huwais |
| 10,980,548 | B2 | 4/2021 | Huwais |
| 2001/0019816 | A1 | 9/2001 | Kumar |
| 2002/0094508 | A1 | 7/2002 | Lorenzi |
| 2004/0223830 | A1 | 11/2004 | Panasik et al. |
| 2004/0230195 | A1 | 11/2004 | Kaikkonen et al. |
| 2005/0118550 | A1 | 6/2005 | Turri |
| 2005/0123364 | A1 | 6/2005 | Zhou |
| 2005/0273110 | A1 | 12/2005 | Boehm et al. |
| 2006/0018733 | A1 | 1/2006 | Dill et al. |
| 2006/0085005 | A1 | 4/2006 | Kenealy et al. |
| 2006/0111724 | A1 | 5/2006 | Ping |
| 2006/0121415 | A1 | 6/2006 | Aldecoa |
| 2006/0127847 | A1 | 6/2006 | Danger et al. |
| 2006/0210949 | A1 | 9/2006 | Stoop |
| 2007/0037117 | A1 | 2/2007 | Jaunberzins |
| 2007/0088362 | A1 | 4/2007 | Bonutti et al. |
| 2009/0136898 | A1 | 5/2009 | Kim |
| 2009/0142731 | A1 | 6/2009 | Kim |
| 2009/0259227 | A1 | 10/2009 | Ahn |
| 2010/0167235 | A1 * | 7/2010 | Vercellotti ......... A61B 17/1615 |
| | | | 433/86 |
| 2010/0266984 | A1 | 10/2010 | Jung |
| 2010/0273128 | A1 | 10/2010 | Aldecoa |
| 2010/0291511 | A1 * | 11/2010 | Lee ....................... A61C 8/0089 |
| | | | 433/215 |
| 2010/0297578 | A1 | 11/2010 | Jaunberzins |
| 2010/0316456 | A1 | 12/2010 | George |
| 2010/0330534 | A1 | 12/2010 | Hyun |
| 2011/0236853 | A1 | 9/2011 | Shimoo |
| 2012/0197311 | A1 | 8/2012 | Kirschman |
| 2012/0244497 | A1 | 9/2012 | Huwais |
| 2013/0218160 | A1 | 8/2013 | Frimanson |
| 2014/0220508 | A1 | 8/2014 | Scalise et al. |
| 2015/0057664 | A1 | 2/2015 | Scianamblo |
| 2015/0097305 | A1 | 4/2015 | Hufschmied |
| 2015/0173776 | A1 | 6/2015 | Burke et al. |
| 2015/0230805 | A1 * | 8/2015 | Huwais ............... A61B 17/1604 |
| | | | 606/80 |
| 2015/0297243 | A1 | 10/2015 | Kulas et al. |
| 2015/0297275 | A1 | 10/2015 | Huwais |
| 2015/0342617 | A1 * | 12/2015 | Kunz ....................... A61C 3/02 |
| | | | 433/215 |
| 2015/0342709 | A1 * | 12/2015 | Huwais ................ A61C 8/0089 |
| | | | 433/173 |
| 2016/0249949 | A1 * | 9/2016 | Voic ........................ A61B 17/16 |
| | | | 606/169 |
| 2017/0071704 | A1 | 3/2017 | Huwais |

FOREIGN PATENT DOCUMENTS

| | | | |
|---|---|---|---|
| CN | 2318985 | 5/1999 | |
| CN | 1246040 A | 3/2000 | |
| CN | 2724645 | 9/2005 | |
| CN | 101229072 A | 7/2008 | |
| CN | 101292906 A | 10/2008 | |
| CN | 102946820 A | 2/2013 | |
| CN | 206745420 U | 12/2017 | |
| DE | 10063333 A1 * | 7/2002 | ............... A61C 3/02 |
| DE | 102004010859 A1 | 4/2005 | |
| DE | 102004010856 A1 | 6/2005 | |
| DE | 102004010858 A1 | 6/2005 | |
| DE | 102004010860 A1 | 6/2005 | |
| EP | 0379201 A2 | 7/1990 | |
| EP | 1273273 A2 | 1/2003 | |
| EP | 1749498 A1 | 2/2007 | |
| EP | 2119403 A1 | 11/2009 | |
| EP | 1752109 B1 | 10/2010 | |
| EP | 3402420 A4 | 9/2019 | |
| FR | 2594684 A | 8/1987 | |
| JP | 10217030 A | 8/1998 | |
| JP | H10217030 | 8/1998 | |
| KR | 101128730 B1 | 3/2012 | |
| KR | 1020150082437 A | 7/2015 | |
| TW | M566058 U | 9/2018 | |
| WO | WO-0209598 A2 * | 2/2002 | ......... A61B 17/1615 |
| WO | 2005011514 A2 | 2/2005 | |
| WO | 2007086622 A1 | 8/2007 | |
| WO | 2011053588 A1 | 5/2011 | |
| WO | WO-2013126569 A1 * | 8/2013 | ........... A61C 1/0069 |
| WO | 2014077920 A1 | 5/2014 | |
| WO | 2015020118 A1 | 2/2015 | |
| WO | 2015138842 A2 | 9/2015 | |
| WO | 2015138842 A3 | 11/2015 | |
| WO | 2015172842 A1 | 11/2015 | |
| WO | 2017124079 A1 | 7/2017 | |
| WO | WO-2018040917 A1 * | 3/2018 | ............ A61B 17/16 |
| WO | 2020210442 A1 | 10/2020 | |

OTHER PUBLICATIONS

Anitua, Ridge expansion with motorized drills, Implant Dialogue, 14 pgs.
Biohorizons, VIP Catalog and Surgical Manual, 2008, 28 pgs.
Biomet Sports Medicine, Bone Dowel Harvester, Copyright 2007, Biomet Sports Medicine, Inc., PO Box 587, Warsaw, IN 46581-0587 (www.biometsportsmedicine.com).

(56) References Cited

OTHER PUBLICATIONS

Calvo-Guarado JL et al., "Compressive osteotomes for expansion and maxilla sinus floor lifting," Med Oral Patol Oral Cir Bucal 2006; 11:E52-5.
Calvo-Guirado JL et al. "Compressive osteotomes for expansion and maxilla sinus floor lifting," Med Oral Patol Oral Cir Bucal 2006;11:E52-5.
Goyal et al., Bone Manipulation Techniques, International Journal of Clinical Implant Dentistry, Jan.-Apr. 2009; 1(1): pp. 22-31.
Lee, Atraumatic Ridge Expansion and Implant Site Preparation with Motorized Bone Expanders, Practical Procedures and Aesthetic Dentistry 2006; 18(1): pp. A-F.
Meisinger, Bone Management catalog, pp. 161-178.
Meisinger, Split-Control, retrieved Mar. 10, 2012 from www.bone-management.com/eng/bm_sortimente_anw_split_eng.htm.
Nishioka, Bone Spreading Technique (Dec. 9, 2010), retrieved Mar. 10, 2012 from www.dentistrytoday.com/implants/4228-bone-spreading-technique, pp. 1-4.
Oxforddictionaries.com. Definition of radial [retrieved on Feb. 25, 2015]. Retrieved from the Internet:http://www.oxforddictionaries.com/us/definition/american_english/radial.
Steier et al., Better horizontal ridge expansion, Dental Tribune I, Sep. 22-28, 2008, pp. 9-10.
Summers, A New Concept in Maxillary Implant Surgery: The Osteotome Technique, Compend Contin Educ Dent, vol. XV, No. 2, pp. 152-160.
www.dentsply-friadent.com, "Ankylos Surgical Manual."
www.nobelbiocare.com, "Validating Innovation: NobelActive Technical and Clinical Story," Nobel Biocare Services AG, 2011.

\* cited by examiner

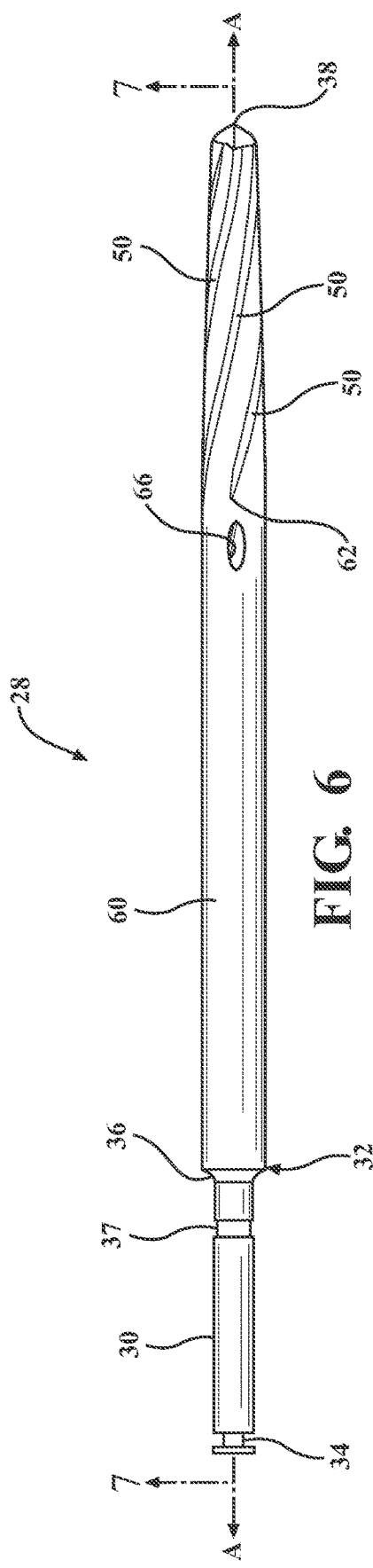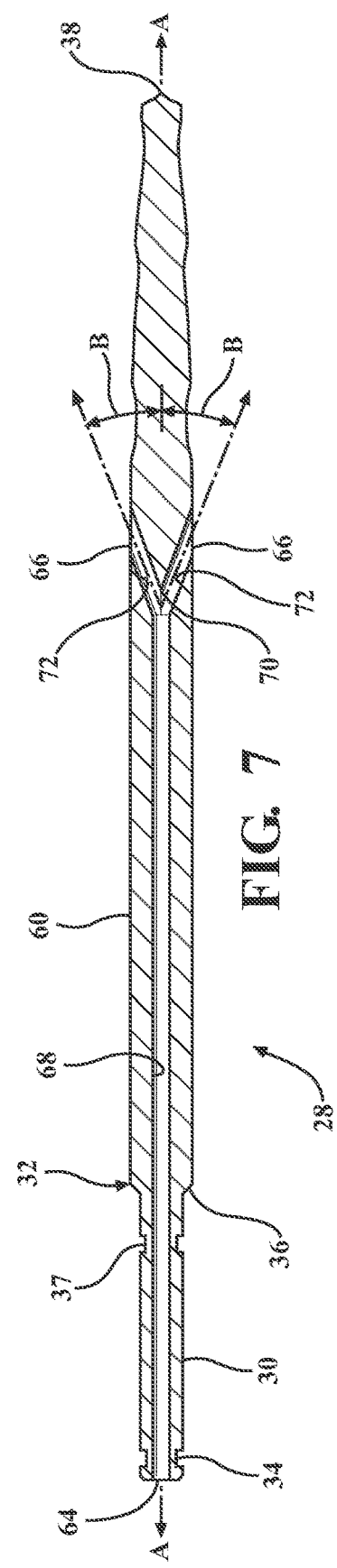

AUTOGRAFTING TOOL FOR DEEP REACH APPLICATIONS

CROSS REFERENCE TO RELATED APPLICATIONS

This application claims priority to U.S. Provisional Patent Application Ser. No. 62/756,406 filed on Nov. 6, 2018, the entire disclosure of which is hereby incorporated by reference and relied upon.

BACKGROUND OF THE INVENTION

Field of the Invention

The invention relates generally to tools for preparing a hole to receive an implant or fixture, and more particularly to rotary osteotomes configured with internal irrigation.

Description of Related Art

An implant is a medical device manufactured to replace a missing biological structure, to support a damaged biological structure, or to enhance an existing biological structure. Bone implants are implants of the type placed into the bone of a patient. Bone implants may be found throughout the human skeletal system, including dental implants in a jaw bone to replace a lost or damaged tooth, joint implants to replace a damaged joint such as a hip or knee, and reinforcement implants installed to repair fractures and remediate other deficiencies, to name but a few.

In some applications, the placement location for the implant is very difficult to access. These so-called "deep reach" situations include (but are not limited to) zygomatic implants like those illustrated in FIG. 1A. A long drill bit or bur in usually needed to prepare the osteotomy to receive the implant as depicted in FIG. 1B. (Please note, the drilling tool shown in FIG. 1B is in accordance with one embodiment of the present invention, and is not admitted prior art.)

Recently, the industry has embraced the osseodensification protocols for preparing an osteotomy. This popular new protocol was pioneered by Dr. Salah Huwais, inventor of this present invention, and has been marketed as a rotary osteotome by Versah, LLC of Jackson, Michigan under the brand name Densah® bur. US Patent Publication 2017/0071704 (Mar. 16, 2017) and PCT Publication WO 2017/124079 (Jul. 20, 2017) describe various examples of the Densah® bur osteotomes and their functionality. The entire disclosures of these publications are hereby incorporated by reference and relied upon in all jurisdictions that recognize incorporation by reference.

A key element of the usage protocol for the Densah® bur osteotome is copious irrigation applied at the external end of the bur, such as by an irrigation-enabled hand piece. Please see FIG. 2. The irrigation fluid is preferably sterile saline solution or water. When a continuous flow of irrigating fluid is provided, the reverse twist of the flutes (in relation to the rotational direction of the osteotome) will have the effect of propelling and pumping the irrigation fluid down toward the bottom of the osteotomy. That is, the flutes transport the irrigating fluid something akin to the vanes of a turbine. As a result, irrigating fluid is forcefully driven toward the bottom of the osteotomy throughout the surgical procedure. This pumping or propelling action is depicted by the downwardly twisting arrows in FIG. 2. A hydraulic pressure is created that pushes outwardly within the osteotomy, as depicted in FIG. 2 as a pressure gradient with small, outwardly pointing arrows. When operated in the densifying mode, the pressure gradient pushes against the bone side walls, preparing and preconditioning the interior surface of the hole. Excess irrigation fluid is exhausted (overflows) out of the osteotomy through the small circular gap that appears around the rotary osteotome when lifted slightly. The pressure gradient will thus increase and decrease in direct response to the amount of force applied by the surgeon as he or she repeatedly advances and relaxes the rotating rotary osteotome into the osteotomy.

By modulating the position of the rotary osteotome in combination with a continuous supply of irrigation fluid, the surgeon can apply an evenly distributed, expansive pressure with piston-like effect to the inner side walls of the osteotomy. This throbbing hydraulic effect has many documented preconditioning advantages, which include: 1) gentle pre-stressing of the bone structure of the osteotomy in preparation for subsequent compacting contact, 2) haptic feedback transmitted through the rotary osteotome that allows the surgeon to tactilely discern the instantaneously applied pressure prior to actual contact between the rotary osteotome and side walls, 3) enhanced hydration of the bone structure which increases bone toughness and increases bone plasticity, 4) hydraulically assisted infusion of bone fragments into the lattice structure of the surrounding bone, 5) reduced heat transfer, 6) hydrodynamic lubricity, 7) dampening or cushioning of the trauma sensed by the patient, and so forth.

However, the aforementioned "deep reach" situations complicate the external irrigation protocol of the Densah® bur osteotome. For example, it can be practically impossible to apply sufficient quantities of irrigating fluid to the flutes of a deeply embedded bur while preparing an osteotomy for a zygomatic implant like those illustrated in FIGS. 1A and 1B.

There is therefore a need for improved tools and techniques that prepare bone and other types of host materials to receive an anchor or implant in "deep reach" applications.

BRIEF SUMMARY OF THE INVENTION

According to a first aspect of this invention a rotary osteotome is configured for deep reach applications. The osteotome comprises a shank that establishes a longitudinal axis of rotation. The shank extends between a drive end and a transition interface. A body extends from the transition interface to an apical end. A plurality of flutes are disposed about the body. Each flute extends from adjacent the apical end to respective terminus. Each flute has a cutting face on one side thereof that defines a rake angle. Each flute also has a densifying face on the other side thereof that defines a heel-side angle. A land is formed between each adjacent pair of flutes. Each land has a working edge along the cutting face of the one adjacent flute. A stopper section of the body is disposed between the terminus of the flutes and the transition interface of the shank. An irrigation conduit passes from the inlet in the shank to the outlet orifice. The outlet orifice is disposed in the stopper section.

According to a second aspect of this invention, a rotary osteotome is configured for deep reach applications. The osteotome comprises a shank that establishes a longitudinal axis of rotation. The shank extends between a drive end and a transition interface. A body extends from the transition interface to an apical end. At least a portion of the body has a conically tapered profile that decreases from a maximum diameter to a minimum diameter adjacent the apical end. A plurality of flutes are disposed about the body. The flutes each extend from adjacent the apical end to a respective terminus. Each flute helically spirals about the conically tapered profile of the body. The plurality of flutes are arranged about the body in equal circumferential increments. Each flute has a cutting face on one side thereof that defines a rake angle and a densifying face on the other side thereof that defines a heel-side angle. A land is formed between each adjacent pair of flutes. Each land has a working edge along the cutting face of the one adjacent the flute. A stopper section of the body is disposed between the terminus of the flutes and the transition interface of the shank. The stopper section is generally cylindrical. An irrigation conduit passes from an inlet in the shank to a plurality of outlet orifices in the stopper section. The inlet is disposed in the drive end of the shank and is aligned along the longitudinal axis. The plurality of outlet orifices are spaced apart from one another in equal circumferential increments about the body.

By locating the outlet orifice(s) on the stopper section of the body, an energetic feed of irrigating fluid is enabled to flow into the flutes and toward the apical end, thus better mimicking external irrigation practices of the prior art. By flowing irrigation fluid into the flutes and toward the apical end, hydraulic effects can be generated with known preconditioning advantages, which include: 1) gentle pre-stressing of the bone structure of the osteotomy in preparation for subsequent compacting contact, 2) haptic feedback transmitted through the rotary osteotome that allows the surgeon to tactically discern the instantaneously applied pressure prior to actual contact between the rotary osteotome and side walls, 3) enhanced hydration of the bone structure which increases bone toughness and increases bone plasticity, 4) hydraulically assisted infusion of bone fragments into the lattice structure of the surrounding bone, 5) reduced heat transfer especially in areas of plastic deformation, 6) hydrodynamic lubricity, and 7) dampening or cushioning of the trauma sensed by the patient, to name a few.

BRIEF DESCRIPTION OF THE SEVERAL VIEWS OF THE DRAWINGS

These and other features and advantages of the present invention will become more readily appreciated when considered in connection with the following detailed description and appended drawings, wherein:

FIG. 6 is a side elevation of a rotary osteotome according to an embodiment of the present invention;

FIG. 7 is a cross-sectional view taken generally along lines 7-7 of FIG. 6;

DETAILED DESCRIPTION OF THE INVENTION

Figure 1A:
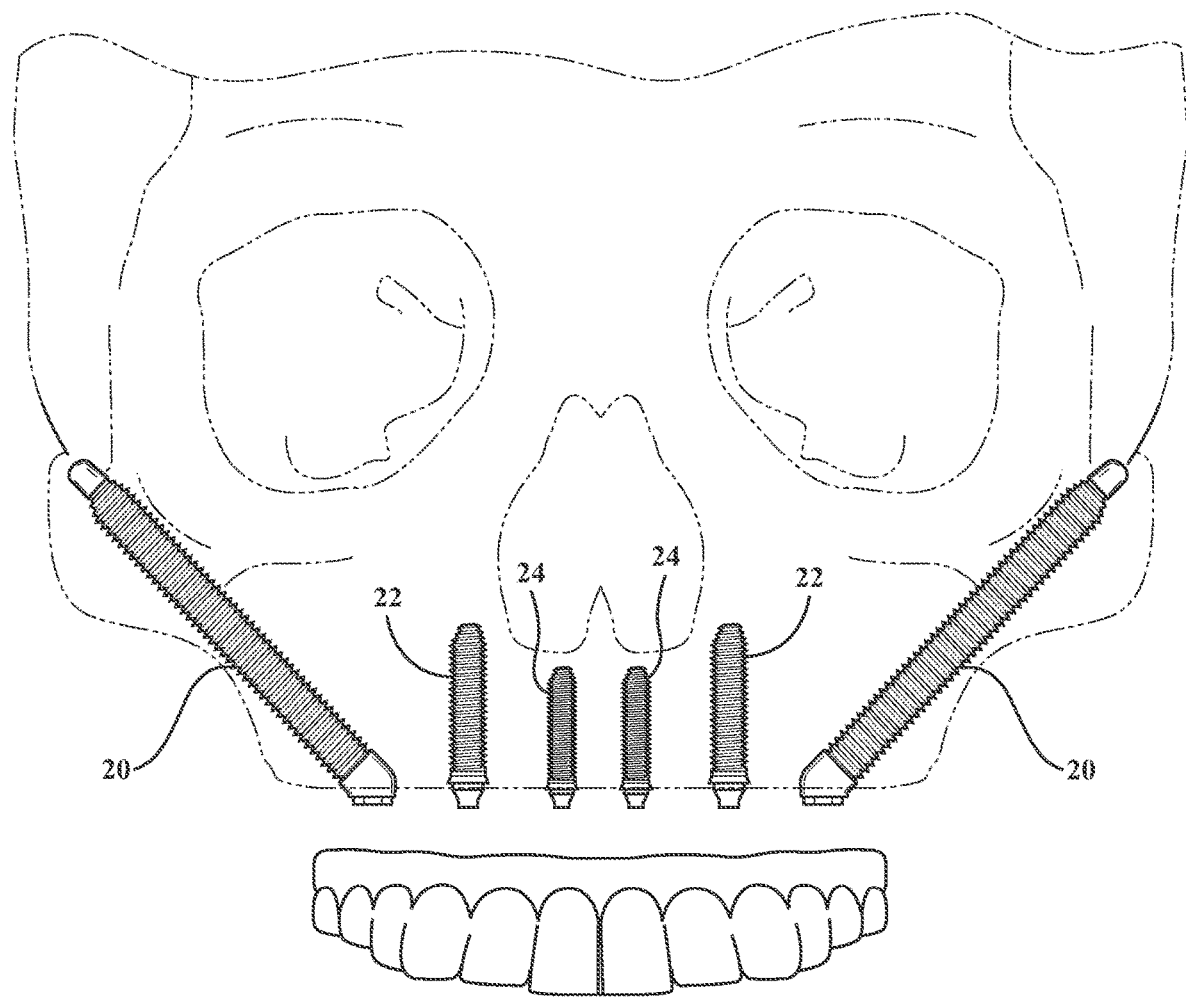
FIG. 1A is an example of a deep reach application in the form of zygomatic implants.
Figure 1B:
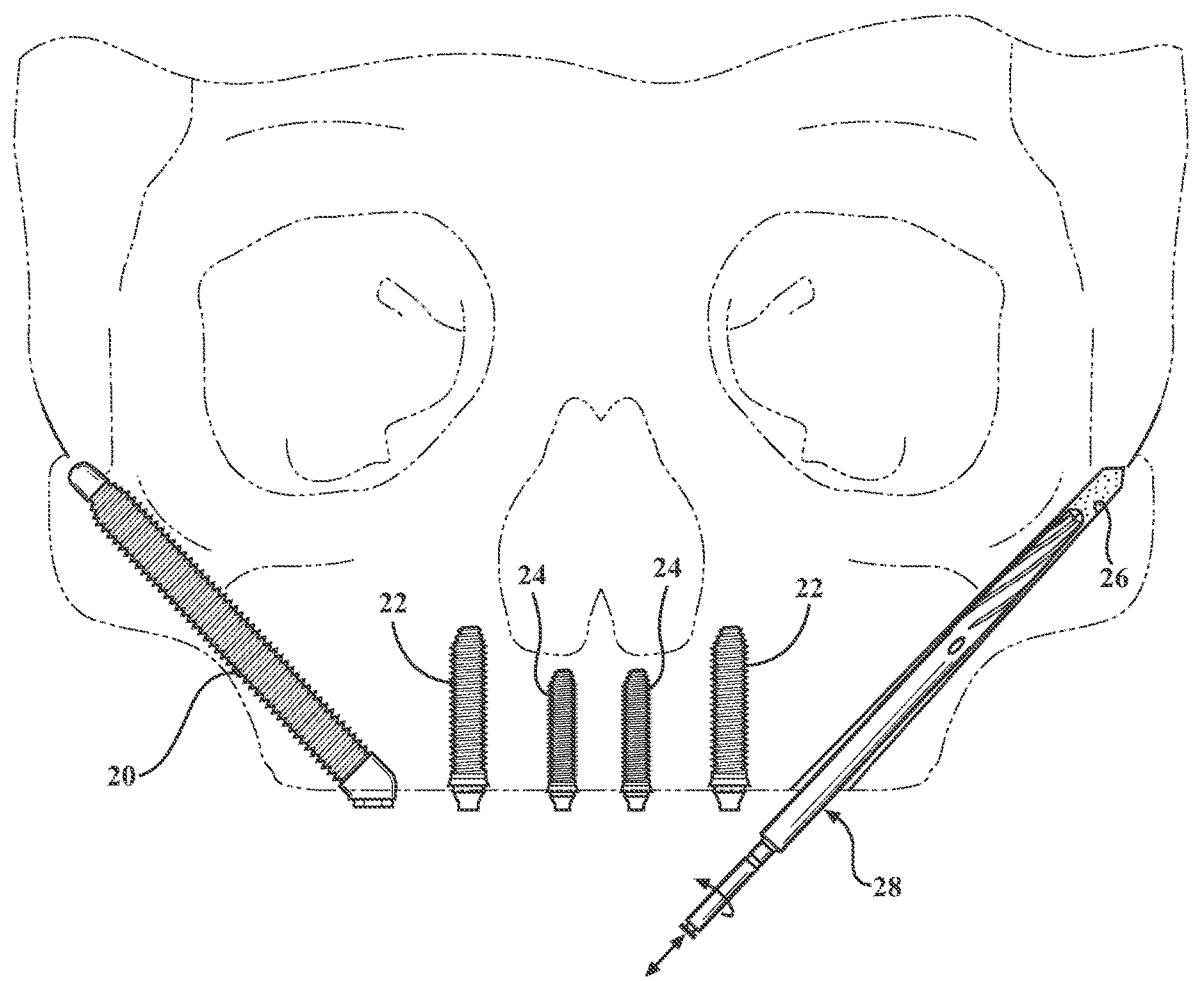
FIG. 1B is a view as in FIG. 1A showing formation of an osteotomy for one of the long implants using a rotary osteotome according to an embodiment of the present invention.

Referring to the figures, wherein like numerals indicate like or corresponding parts throughout the several views, FIGS. 1A and 1B show examples of dental implants, in which preparation of osteotomies are required to receive a bone implant 20, 22 or 24. It will be understood that this invention is not limited to dental applications, but may be applied across a wide spectrum of orthopedic applications. Human applications are typical, but animal applications are equally plausible and not outside the scope of this invention. Furthermore, the invention is not limited to bone applications, but may be used to prepare holes in organic materials like wood as well as in non-organic materials for industrial and commercial applications, including but not limited to metal foam and other cellular materials to name but a few.

Figure 2:
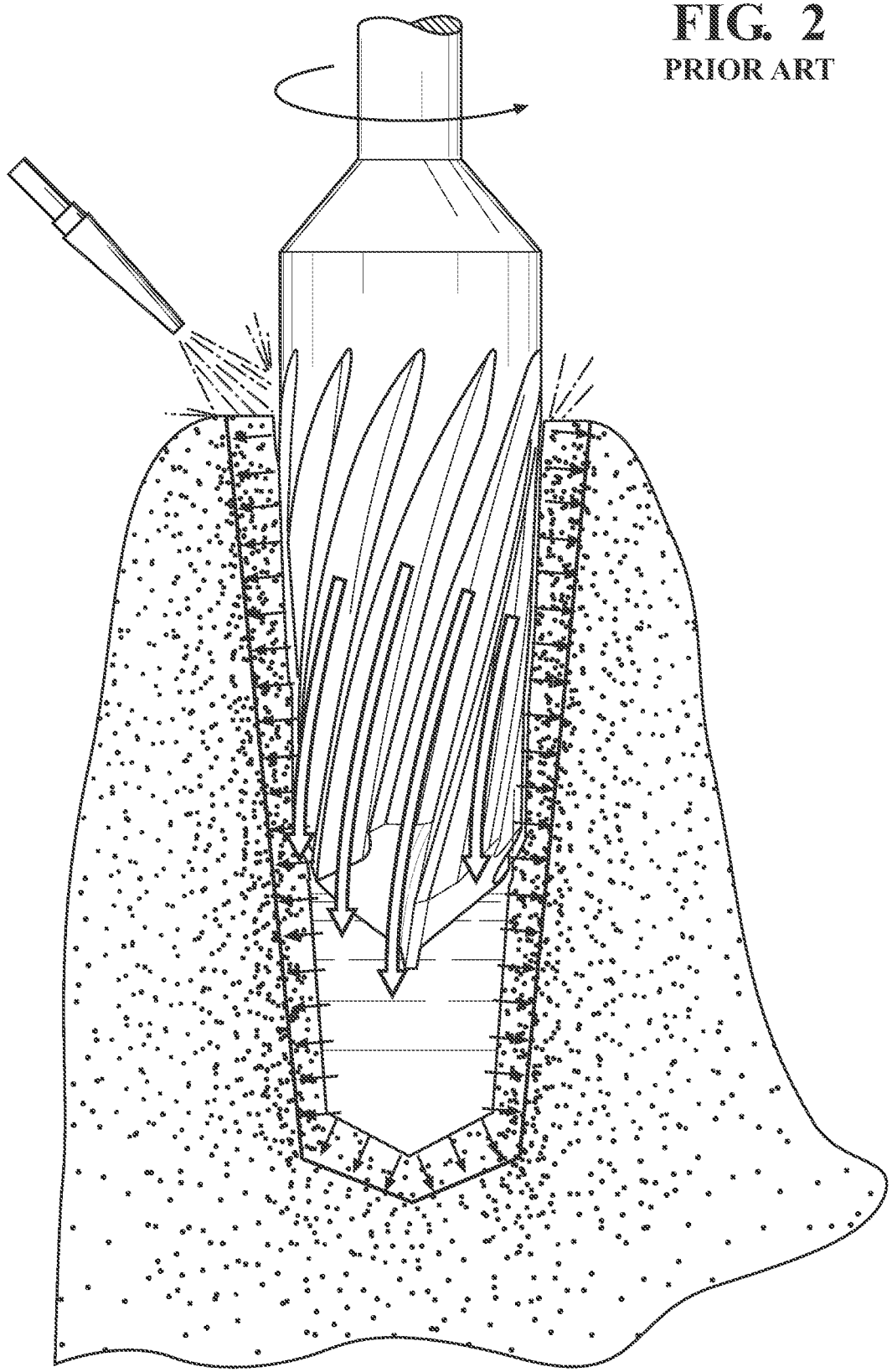
FIG. 2 shows a prior art rotary osteotome configured for external irrigation, copied directly from US Patent Publication 2017/0071704.

For illustrative purposes only, the externally irrigated prior art style rotary osteotome of FIG. 2 can be useful to explain the manner in which an expanded and near final fully formed osteotomy 26 can be prepared to receive an implant or other fixture. Once the osteotomy 26 has been prepared, the implant or fixture screw is screwed into place (e.g., implant 20, 22, 24 in FIG. 1). A series of steps are required to accomplish the fully formed osteotomy 26, which include first boring a pilot hole into the recipient bone to form the initial osteotomy, then incrementally expanding the osteotomy 26 using progressively wider rotary expander devices or osteotomes until final intended diameter and depth are achieved. This sequential expansion method is well-suited for the externally irrigated prior art style rotary osteotome (FIG. 2) as well as for the novel, internally irrigated rotary osteotome of this present invention.

Turning now to FIGS. 3-15, a rotary osteotome 28 according to an embodiment of this invention is shown including a shank 30 and a body 32. The shank 30 has an elongated cylindrical shaft that establishes a longitudinal axis of rotation A for the rotary osteotome 28. A drill motor engaging coupling 34 is formed at the distal upper end of the shaft for connection to the drill motor (not shown). The particular configuration of the coupling 34 may vary depending on the type of drill motor used, and in some cases may even be merely a smooth portion of the shaft against which the jaws of a collet grip. The body 32 joins to the lower end of the shank 30, which joint may be formed with a tapered or domed transition 36. In some cases, the shank 30 may include an annular groove 37 disposed a predetermined distance from the transition interface 36. The groove 37 can be used to locate a depth stop (not shown) used to limited the depth of penetration for the osteotome 28.

A lower portion of the body 32 preferably has conically tapered profile decreasing from a maximum diameter to a minimum diameter adjacent an apical end 38. However, in some contemplated embodiments the lower end of the body 32 may be non-tapered (i.e., cylindrical). The apical end 38 is thus remote from the shank 30. Preferably, all osteotomes 36 in a kit will have the same taper angle, or approximately the same taper angle. Taper angles between about 1° and 5° (or more) are possible depending upon the application. More preferably, taper angles between about 2°-3° will provide satisfactory results. And still more preferably, a taper angle of about 2° 36' is known to provide outstanding results for dental applications.

Figure 10:
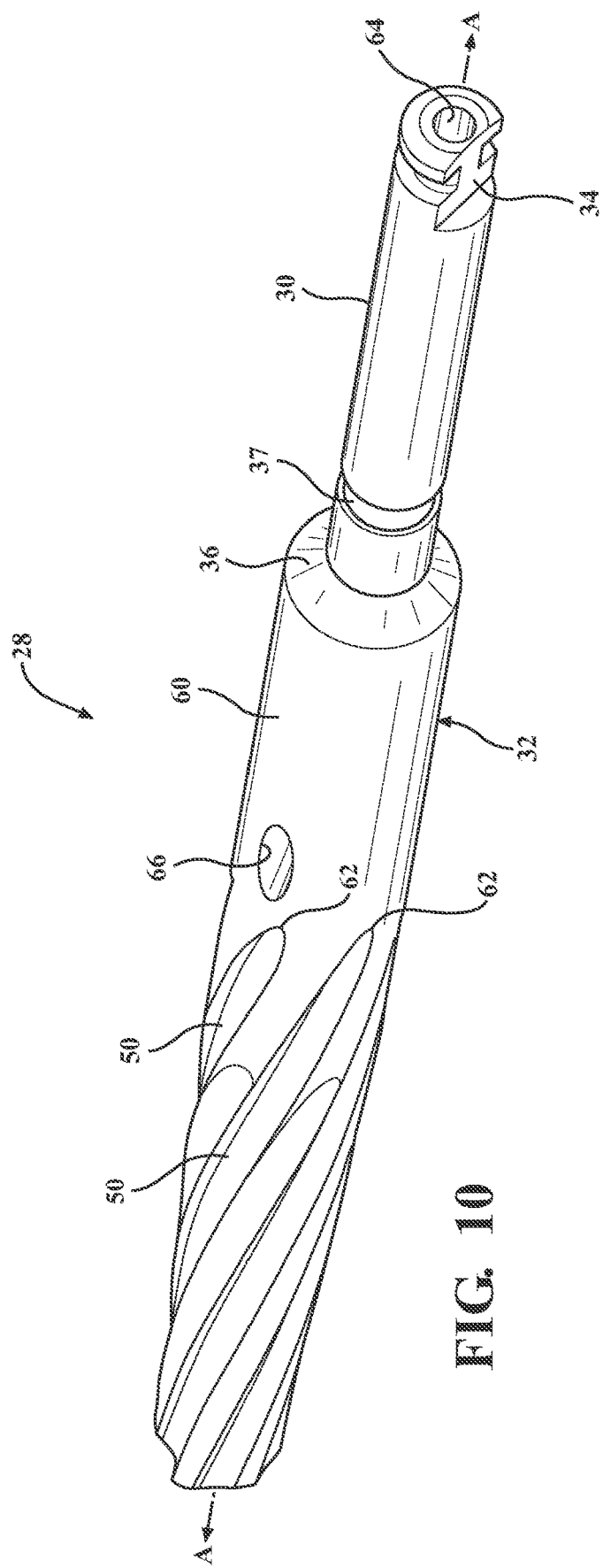
FIG. 10 is a perspective view of a rotary osteotome according to an embodiment of the present invention.

The apical end 38 is defined by at least one, but preferably a pair of lips 40 best seen in FIG. 10. The lips 40 are edges disposed on opposite sides of the apical end 38, and in the illustrated embodiment do not lie within a common plane. In other words, as shown the lips 40 may be slightly offset (in terms of a direct diametrical alignment) by the short length of a chisel point 42 extending centrally through the longitudinal axis A. The chisel point 42 is a common feature found in drilling tools, but alternative apical end 38 formations to the chisel point 42 are of course possible, including rounded and simple pointed shapes, etc. As mentioned, the lips 40 are edges that angle upwardly and outwardly (radially) from the apical end 38. The angle of the lips 40 may be varied to optimize performance for the application. Lip 40 angles relative to the longitudinal axis A may range between about 30° (very pointed) and 75° (very blunt). In the illustrated examples, the lip angle is approximately 60° measured relative to longitudinal axis A, or 120° measured between the two opposing lips 40.

Each lip 40 has a generally planar first trailing flank 44. The first trailing flanks 44 are canted from their respective lips 40 at a first angle. The first angle may be varied between about 30° and 60° to optimize performance for the application. In practice, the first angle may be approximately 45° measured relative to longitudinal axis A. It will be appreciated therefore that the two opposing first trailing flanks 44 are set in opposite directions so that when the rotary osteotome 28 is rotated in use, the first trailing flanks 44 either lead or follow their respective lips 40. When first trailing flanks 44 lead their respective lips 40, the osteotome 28 is said to be turning in a non-cutting direction for the densifying mode; and conversely when the first trailing flanks 44 follow their respective lips 40, the osteotome 28 is said to be turning in a cutting direction where the lips 40 cut or slice bone on descent. In the densifying direction, the first trailing flanks 44 form, in effect, a large negative rake angle for the lips 40 to minimize chip formation and shear deformation in the bone (or other host material) at the point of contact with the lips 40.

A generally planar second trailing flank 46 is formed adjacent to, and falls away from, each first trailing flank 44 at a second angle. The second angle is smaller than the first angle, preferably less than about 55°. In an example where the first trailing flanks 44 are formed at 45° (relative to the axis A), the second trailing flanks 46 may be 40° or less. A generally planar relief pocket 48 is formed adjacent to, and falls away from, each second trailing flank 46 at a third angle. The third angle is smaller than the second angle. In an example where the second trailing flanks 46 are formed at 40° (relative to the axis A), the relief pockets 48 (i.e., the third angle) may be 30° or less. Each relief pocket 48 is disposed in a sector of the apical end 38 between a second trailing flank 46 and a lip 40. When the rotary osteotome 28 is rotated in the cutting direction, a significant amount of bone chips collect in the relief pocket 48 regions. When the rotary osteotome 28 is rotated in the densifying direction, little to no bone chips collect in the relief pocket 48 regions.

A plurality of grooves or flutes 50 are disposed about the body 32. The flutes 50 may or may not have common axial length and radial depths. I.e., it is possible that the flutes 50 could, in some configurations, not all be identical. The flutes 50 are preferably, but not necessarily, equally circumferentially arranged about the tapered lower end of the body 32. The diameter of the body 32 may influence the number of flutes 50. As an example, bodies 42 in the range of about 1.5-2.5 mm may be formed with three or four flutes; bodies 42 in the range of about 2.0-3.0 mm may be formed with five or six flutes; bodies 42 in the range of about 3.0-4.0 mm may be formed with seven or eight flutes. And so on. Of course, the number of flutes 50 may be varied more or less than the examples given in order to optimize performance and/or to better suit the particular application.

In the illustrated embodiment, the flutes 50 are formed with a helical twist. If the cutting direction is in the right-hand (clockwise) direction, then preferably the helical spiral is also in the right-hand direction. This RHS-RHC configuration is shown throughout the Figures, although it should be appreciated that a reversal of cutting direction and helical spiral direction (i.e., to LHS-LHC) could be made if desired with substantially equal results.

Each flute 50 has a densifying face 52 and an opposing cutting face 54. A rib or land is formed between adjacent flutes 50, in alternating fashion. Thus, a four-flute 50 rotary osteotome 28 will have four lands, a six-flute 50 rotary osteotome 28 will have six interleaved lands, and so forth. Each land has an outer land face 56 that extends (circumferentially) between the densifying face 52 of the flute 50 on one side and the cutting face 54 of the flute 50 on its other side. The sharp interface between each land face 56 and its associated cutting face 54 is referred to as a working edge 58. Depending on the rotational direction of the rotary osteotome 28, the working edge 58 either functions to cut bone or compact bone. That is, when the osteotome 28 is rotated in the cutting direction, the working edges 58 slice and excavate bone (or other host material). When the osteotome 28 is rotated in the densifying (non-cutting) direction, the working edges 58 compress and radially displace bone (or other host material) with little to no cutting whatsoever. This compaction and radial displacement is exhibited as gentle pushing of the osseous structure laterally outwardly in a condensation mechanism.

Figure 3:
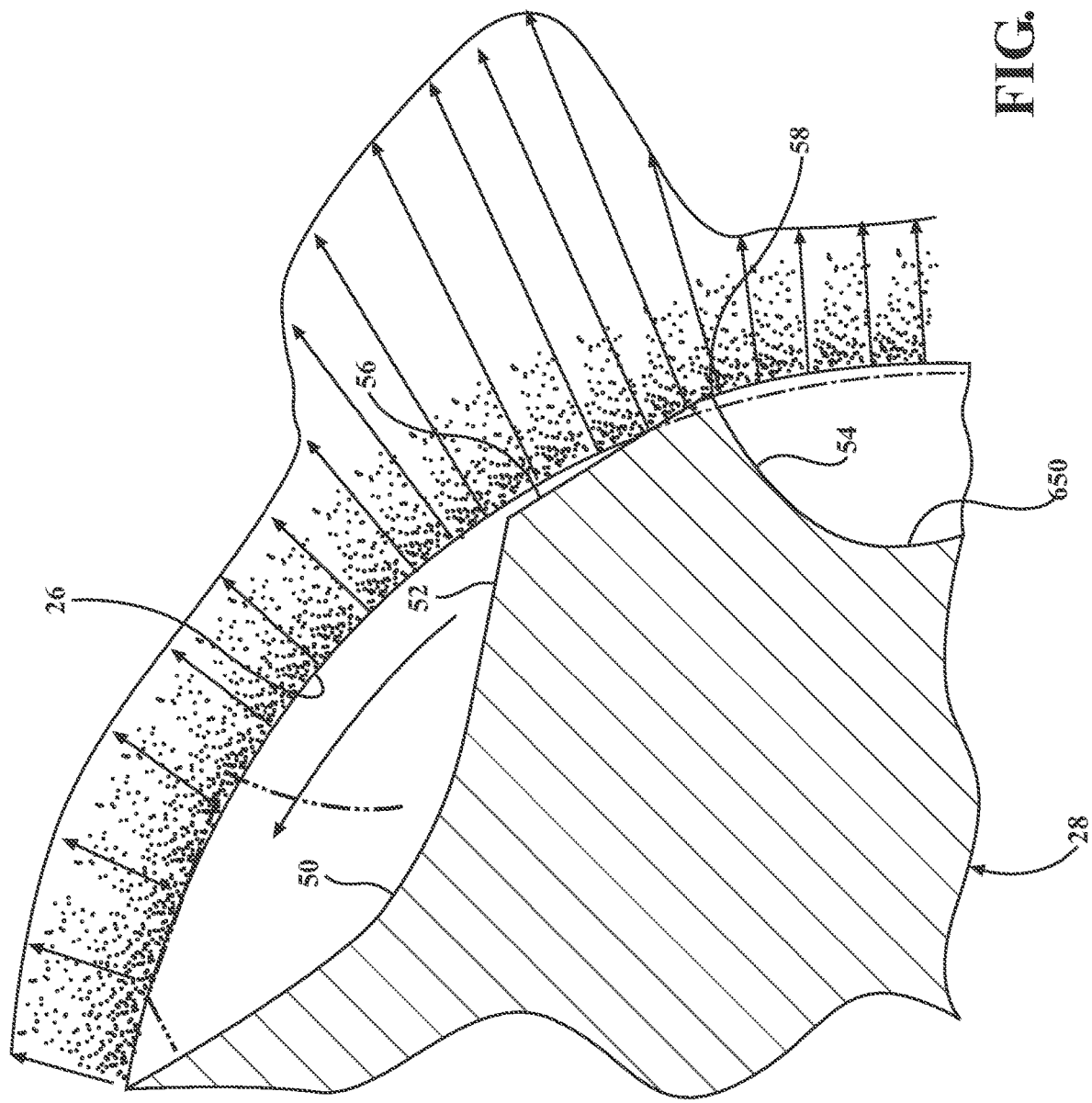
FIG. 3 is a fragmentary cross-sectional view showing the elevated hydrodynamic pressure spike generated against the bone sidewall immediately prior to contact with a working edge.
Figure 9:
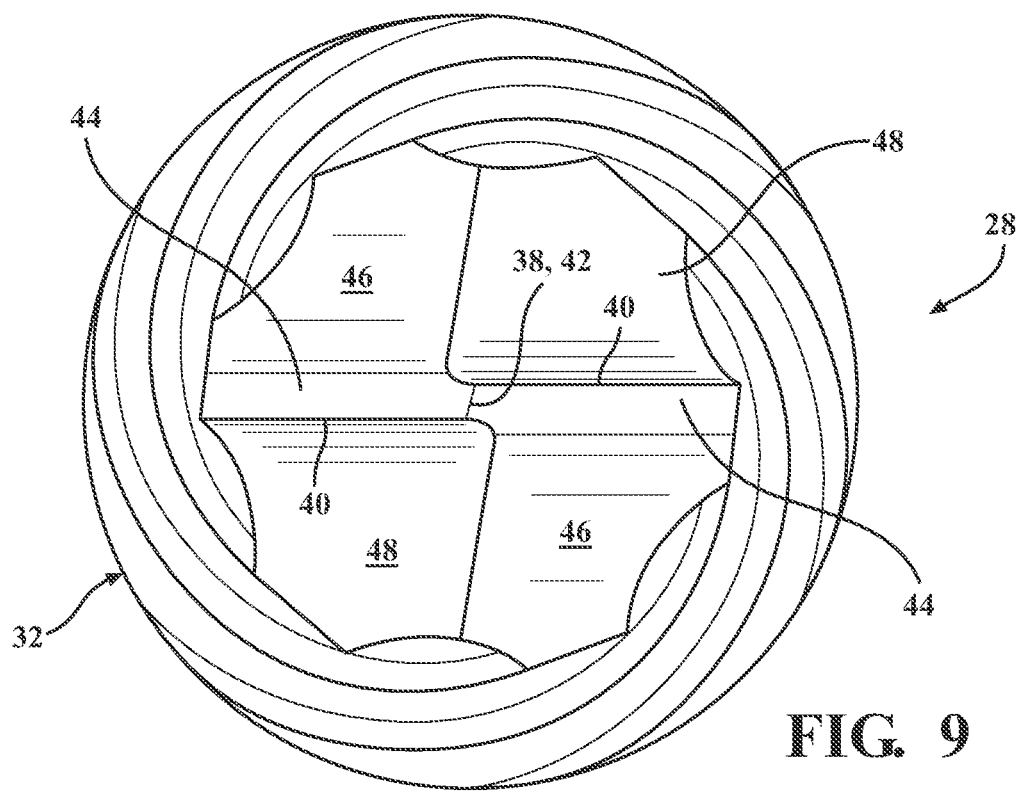
FIG. 9 is an end view from the perspective of the apical end.

The working edges 58 are shown throughout the illustrations as being substantially margin-less, in that the entire portion of each land face 56 is cut away behind the working edge 58 to provide complete clearance as can be appreciated from the in-use depiction of FIG. 3. As mentioned above in connection with the angle of the helical twist, the substantially margin-less working edges 58 are shown turning away from the densifying direction as the conically tapered profile portion of the body 32 decreases in diameter. In other words, when the densifying direction is counter-clockwise (see directional arrow in FIG. 5), the helical twist of the working edges 58 winds in the counter-clockwise direction when viewed from the top of the body 32 looking toward its apical end 38. Or conversely, as shown in FIG. 9 when viewed from the apical end 38 looking toward top of the body 32, the twist will appear to be in the clockwise direction. Thus, when the densifying direction is counter-clockwise, the working edges 58 will turn away from the densifying direction when all of the land faces 56 and flutes 50 orbit counter-clockwise about the longitudinal axis A as one traces each land face 56 and flute 50 downwardly toward the apical end 38.

The cutting face 54 establishes a rake angle for each respective working edge 58. A rake is an angle of slope measured from the leading face of the working edge 58 to an imaginary line extending perpendicular to the surface of the worked object (e.g., inner bone surface of the osteotomy). See FIG. 3. Rake angles can be: positive, negative or zero. According to FIG. 3, the rake angle for working edge 58 when rotated in a cutting direction is preferably zero or negative provided a crisp cutting edge 58 is established that will be well-suited to cut/slice bone when the rotary osteotome 28 is rotated in the cutting direction. In practice, it has been discovered that the cutting functionality of the rotary osteotome 28 can be optimized when the rake angle of the cutting face 54 is between about 0° and about −65° (negative rake), which may vary as a function of distance from the apical end 38. The same or generally the same negative rake angle may be maintained along the entire length of the flute 50. Intentional changes in the rake angle can be regressive or progressive. A progressive change would indicate that the rake angle is at its smallest (closest to zero) adjacent the apical end 38 and grows smoothly to a maximum adjacent the stopper section 60. A regressive change, on the other hand, would mean the negative rake angle is larger at the apical end 38 and grows smaller (and thus more aggressive in cutting mode) near the stopper section 60.

When the rotary osteotome 28 is counter-rotated, in the densifying mode, the effective rake angle is established between the working edge 58 and the land face 56, which may lie at a large negative rake angle in the order of about 55°-89°. The large negative rake angle of the working edge 58, when rotated in a densifying direction, applies outward pressure at the point of contact between the wall of the osteotomy 26 and the working edge 58 to create a compression wave ahead of the point of contact. Osseodensification may also be loosely compared to the well-known process of burnishing metal to improve metal surface quality.

Downward pressure applied by the surgeon is needed to keep the working edge 58 in contact with the bone surface of the osteotomy 26 being expanded. That is, pressure is needed to generate and propagate a compression wave in the bone that begins when the contact stresses exceed the yield strength of the host bone material. This is aided by the taper effect of the osteotomy 26 and tool 28 to create lateral pressure (i.e., in the intended direction of expansion). The harder the surgeon pushes the rotary osteotome 28 into the osteotomy 26, the more pressure is exerted laterally. This gives the surgeon complete control of the expansion rate irrespective to a large degree on the rotation speed of the rotary osteotome 28, which is a factor underlying the short learning curve required to master the osseodensification technique. Thus, the compaction intensity depends chiefly on the amount of force exerted on the rotary osteotome 28, which is controlled by the surgeon. The more force exerted; the quicker expansion will occur.

As each working edge 58 drags across the bone, the applied forces can be decomposed into two components: one normal to the bone's surface, pressing it outwardly, and the other tangential, dragging it along the inner surface of the osteotomy 26. As the tangential component is increased, the working edge 58 will start to slide along the bone. At the same time, the normal force will deform the softer bone material. If the normal force is low, the working edges 58 will rub against the bone but not permanently alter its surface. The rubbing action will create friction and heat, but this can be controlled by the surgeon by altering, on-the-fly, the rotation speed and/or pressure and/or irrigation flow. Because the lower portion of the body 32 is tapered, the surgeon may at any instant during the surgical procedure lift the working edges 58 away from contact with the surface of the bone to allow cooling. This can be done in a controlled "bouncing" fashion where pressure is applied in short bursts with the surgeon continuously monitoring progress and making fine corrections and adjustments. As the surgeon-applied downward force increases, eventually the stresses in the bone surface exceed its yield strength. When this happens, the working edges 58 will plow through the surface and create a trough behind. The plowing action of the working edges 58 thus progressively enlarges the osteotomy until the rotary osteotome 28 reaches full/maximum depth, at which time a different larger rotary osteotome 28 must be used to achieve further expansion if desired.

While the elastic properties of bone are well-known, if the load imposed by the surgeon does not exceed the bone's ability to deform elastically, the bone will promptly return to its initial (un-deformed) condition once the stress is removed. On the other hand, if the load imposed by the surgeon exceeds the bone's ability to deform elastically, the bone will deform and change shape permanently by plastic deformation. In bone, the permanent change in shape may be associated with micro-cracks that allow energy release, a compromise that is a natural defense against complete fracture. If these micro-cracks are small, the bone remains in one piece while the osteotomy expands. The region of plastic deformation extends from the yield point of the material, all the way to the point of fracture. The peak of the curve between yield point and fracture indicates the material's ultimate tensile strength. When a material (e.g., bone) is subjected to stress in the region between its yield point and its ultimate tensile strength, the material experiences strain hardening. Strain hardening, also known as work hardening or cold working, is the strengthening of a ductile material by plastic deformation. This strengthening occurs because of dislocation movements and dislocation generation within the crystal structure of the material—which for bone materials corresponds with the dislocation of the cross-links between collagen fibers in the bone tissue. The material tends to experience necking when subjected to stress in the region between its ultimate tensile strength and the point of fracture.

The direction of helical twist can be designed to play a role in contributing to the surgeon's control so that an optimum level of stress (in the strain hardening zone) can be applied to the bone (or other host material) throughout the expansion procedure. In particular, the RHS-RHC configuration described above, which represents a right-hand spiral for a right-hand cutting direction (or alternatively an LHS-LHC configuration, not shown) applies a stress that provokes a beneficial opposing axial reaction force ($R_y$) in the host bone when the rotary osteotome 28 is continuously rotated at high speed in a densifying direction and concurrently forcibly advanced (manually by the surgeon) into an osteotomy 26. This opposing axial reaction force ($R_y$) is illustrated graphically in FIG. 4 as being directionally opposite to the forcibly advanced direction into the osteotomy 26. In other words, if the surgeon operating the rotary osteotome 28 is pushing the rotary osteotome 28 downwardly into an osteotomy 26, then the opposing axial reaction force ($R_y$) works in the opposite direction to push the osteotome upwardly. The opposing axial reaction force ($R_y$) is the vertical (or perhaps more accurately the "axial" vis-à-vis the longitudinal axis A) component of the reaction force that is the Newtonian "equal and opposite reaction force" applied by the bone against the full length of the working edges 58 of the rotary osteotome 28. An opposing axial reaction force ($R_y$) is also created by the effectively large negative rake angle at the lips 40 when the rotary osteotome 28 is rotated in a densifying direction. Those of skill in the art will appreciate alternative embodiments in which the opposing axial reaction force ($R_y$) is created by either the configuration of the lips 40 alone or of the working edges 58 alone rather than by both (40, 58) acting in concert.

For a surgeon to advance the apical end 38 toward the bottom of the osteotomy 26 when the rotary osteotome 28 is spinning in the densifying direction, he or she must push against and overcome the opposing axial reaction forces ($R_y$) in addition to supplying the force needed to plastically displace/expand the bone as described above. The rotary osteotome 28 is designed so that the surgeon must continually work, as it were, against the opposing axial reaction forces ($R_y$) to expand the osteotomy 26 by compaction, i.e., when in the densifying mode. Rather than being a detriment, the opposing axial reaction forces ($R_y$) are a benefit to the surgeon by giving them greater control over the expansion process. Because of the opposing axial reaction forces ($R_y$), the rotary osteotome 28 will not be pulled deeper into the osteotomy 26 as might occur with a standard "up cutting" twist drill or burr that is designed to generate a tractive force that tends to advance the osteotome toward the interior of the osseous site. Up-cutting burrs have the potential to grab and pull the burr more deeply into the osteotomy, which could lead to inadvertent over-penetration.

In the densifying mode, the intensity of the opposing axial reaction forces ($R_y$) is always proportional to the intensity of force applied by the surgeon in advancing the body 32 into the osteotomy 26. This opposing force thus creates real-time haptic feedback that is intuitive and natural to inform the surgeon whether more or less applied force is needed at any given instant. This concurrent tactile feedback takes full advantage of the surgeon's delicate sense of touch by applying reaction forces (R, and in particular the axial component $R_y$) directly through the rotary osteotome 28. In this densifying mode, the mechanical stimulation of the opposing axial reaction forces ($R_y$) assists the surgeon to better control the expansion procedure on the basis of how the bone (or other host material) is reacting to the expansion procedure in real time.

Thus, the controlled "bouncing" or "pumping" action described above is made more effective and substantially more controllable by the opposing axial reaction forces ($R_y$) so that the surgeon can instinctively monitor progress and make fine corrections and applied pressure adjustments on-the-fly without losing control over the rate of expansion. The tactile feedback from the opposing axial reaction forces ($R_y$) allows a surgeon to intuitively exert stress on the bone material so that its strain response preferably resides in the strain hardening zone, that is, between its yield point to its ultimate tensile strength. In any event, the surgeon will endeavor to maintain the stress (as generated by the force he or she applies through the rotating rotary osteotome 28) above the elastic limit and below the point of fracture. Of course, until the applied stress passes the elastic limit, the bone will not permanently deform at all; and to apply stress beyond the point of fracture will cause the bone (or other host material) to break—possibly catastrophically.

Figure 4:
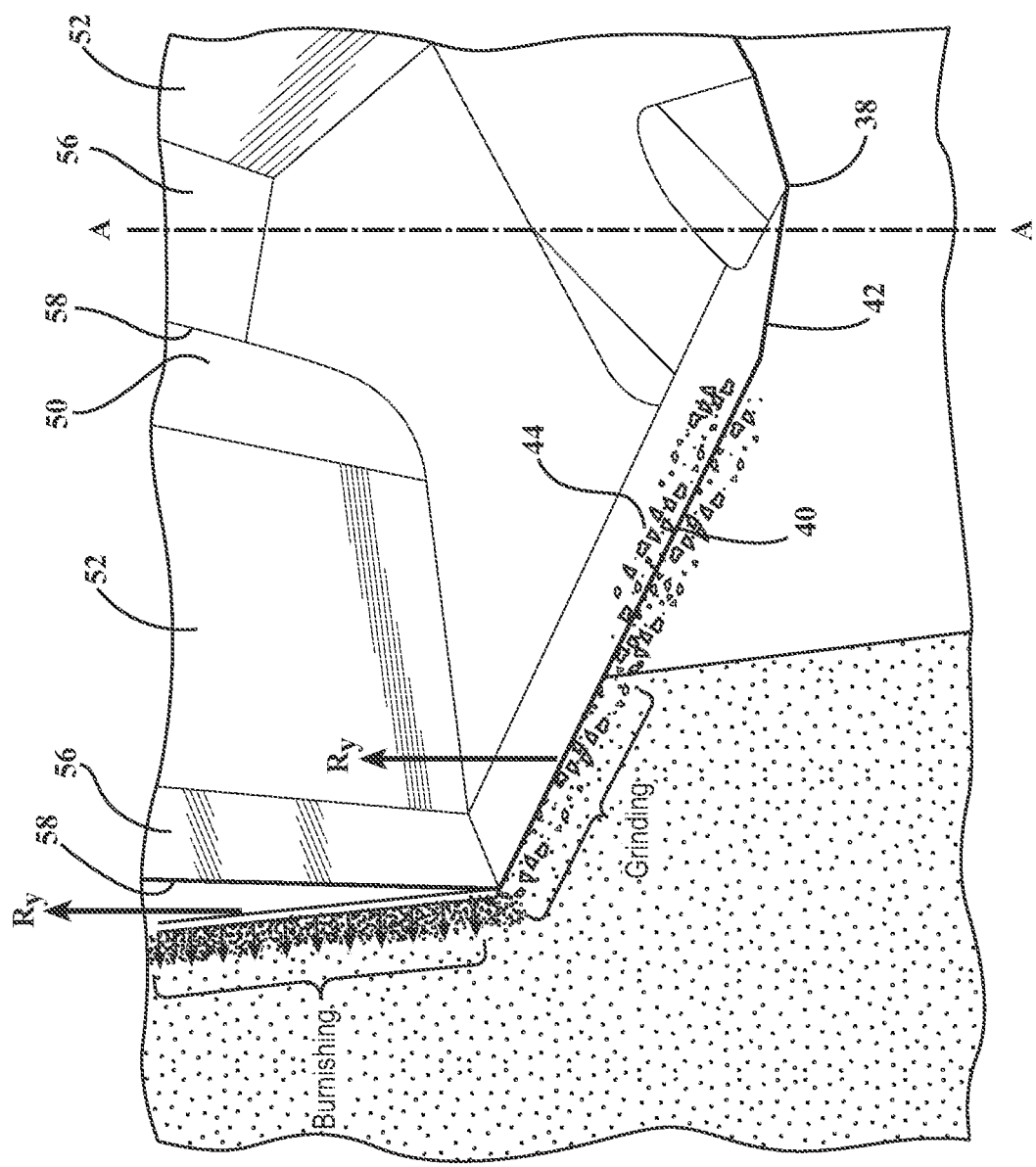
FIG. 4 is an enlarged view depicting the bone grinding and auto-grafting features of the apical end.
Figure 5:
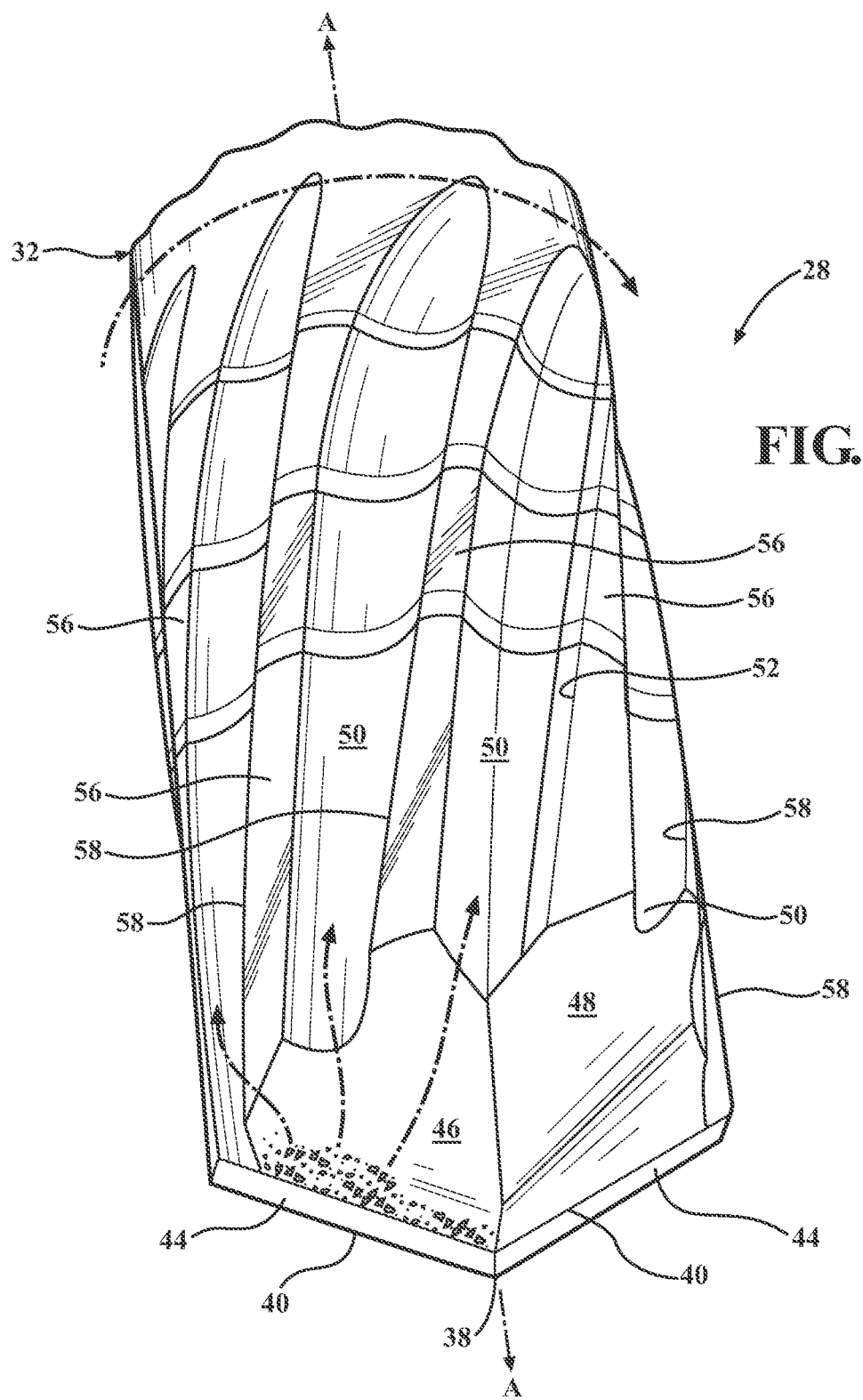
FIG. 5 is a fragmentary perspective view of the apical end illustrating the region of the apical end where bone material collects and is subsequently directed into the flutes for repatriation into surrounding bone.
Figure 8:
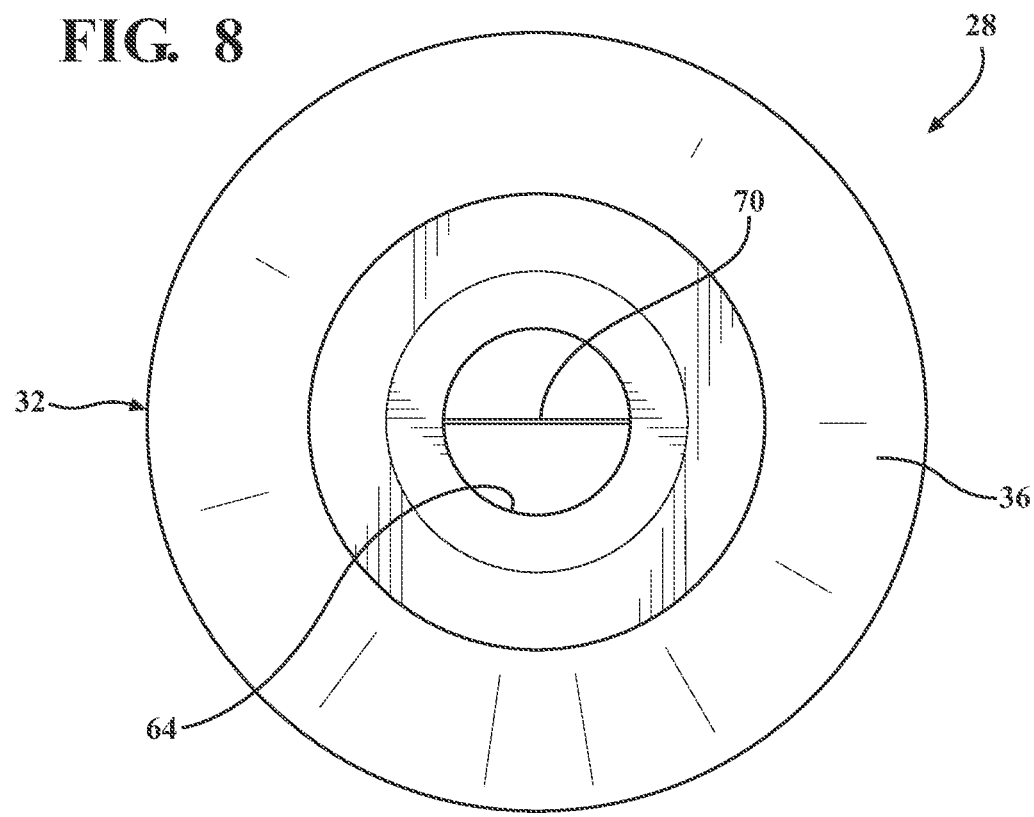
FIG. 8 is an end view from the perspective of the drive coupling of the shank.

FIGS. 4 and 5 illustrate the ability of the rotary osteotome 28 to simultaneously auto-graft and compact bone. The compaction aspect may be defined as the gentle push of osseous structure laterally outwardly to compact the cells throughout the region surrounding the osteotomy 26. The rotary osteotome 28 is configured to simultaneously auto-graft and compact the small quantities of ground/milled bone resulting from each larger size osteotome 28 as it is rotated and forcibly advanced into the osteotomy 26. The auto-grafting phenomena supplements the basic bone compaction and condensation effects described above to further densify the inner walls 82 of the osteotomy. Furthermore, auto-grafting—which is the process of repatriating the patient's own bone material—enhances natural healing properties in the human body to accelerate recovery and improve osseointegration.

FIG. 4 shows an enlarged view of the interface between the apical end 38 and the host bone material at the point where the outermost edge of each rotating and forcibly advancing lip 40 contacts the bone. Attrition causes the bone to be ground away. The bone debris collects mainly on the second trailing flanks 46, i.e., immediately behind the respective first trailing flanks 44. Some of the accumulated bone debris migrates radially inwardly along the lips 40 and is carried all the way to the very bottom of the osteotomy 26. The remainder of the accumulated bone debris is distributed along the plurality of flutes 50 that directly intersect the second trailing flanks 46 by the pressure exerted through the surgeon's manual pushing efforts. This is illustrated in FIG. 5. Observe that a plurality of flutes 50 open into the second trailing flanks 46 for receiving an up-flow of boney slurry in densifying mode. These flutes 50 readily carry bone debris away from the grinding interface, thereby reducing the possibility of heat- and/or pressure-induced necrosis in the bone particles.

Mixed with blood and collagen and irrigating fluid, the bone chips have the consistency of a semi-viscous slurry. Bone debris that is distributed up the flutes 50 works its way toward the associated land faces 56 where it is wiped and pressed into the cellular walls of the osteotomy 26 and immediately grafted back into the patient's bone very near to the sight were it was harvested. Bone debris that is carried to the bottom of the osteotomy 26 is wiped and pressed into the bottom of the osteotomy 26. As a result, an auto-grafting zone is developed around and under the compaction region. And at the osteotomy bottom, where this is little-to-no compaction at all, there is a significant zone of auto-grafting which serves to densify and positively stimulate an area of the osteotomy 26 which could otherwise not be densified. The osseodensification method thus preserves bone and its collagen content to enhance plasticity. The osseodensification method allows for enlarging an osteotomy 26 by compacting (and/or by cutting when rotation is reversed) with a rotary osteotome 28 in preparation for a subsequently placed implant or fixture.

Figure 11:
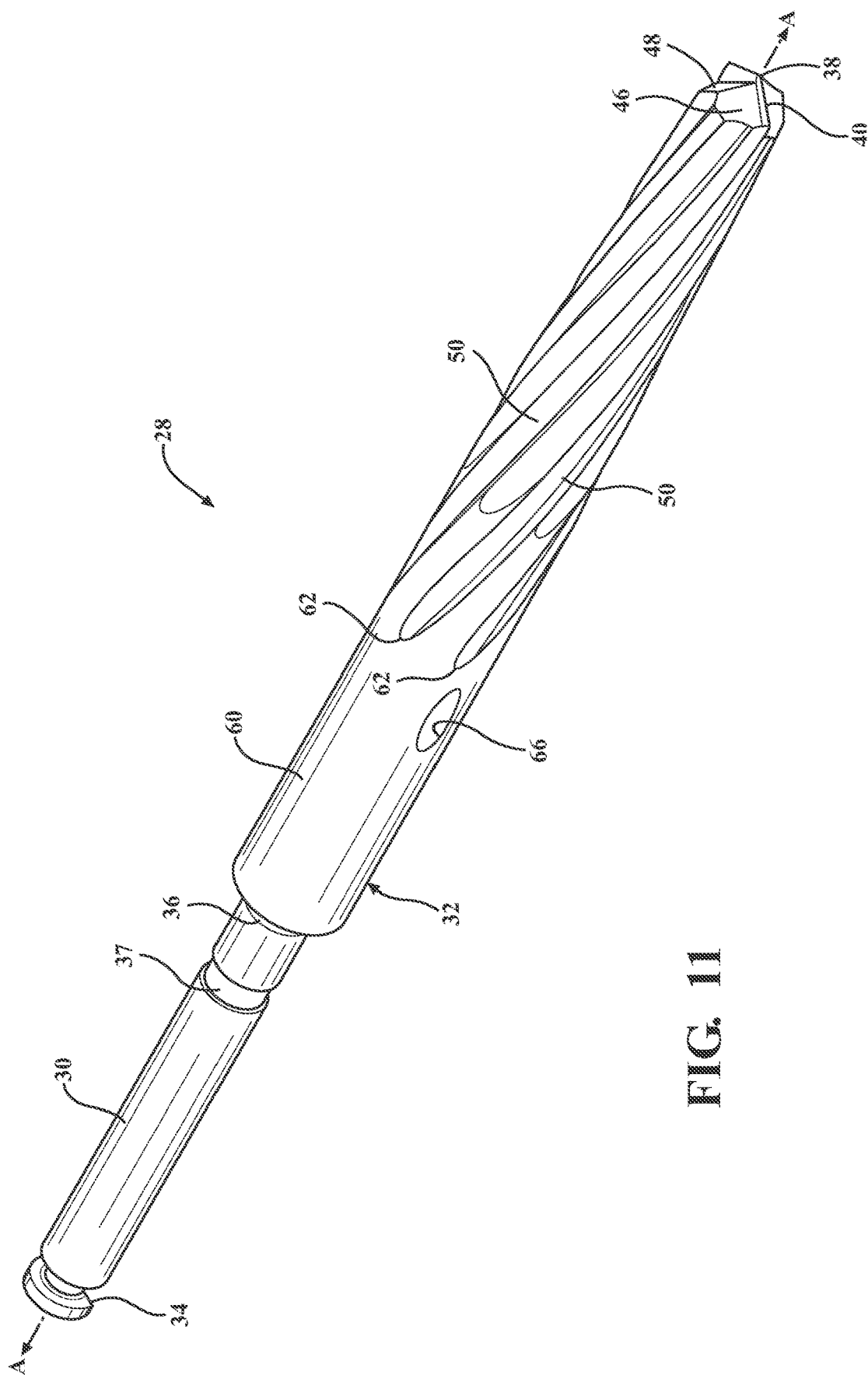
FIG. 11 is a perspective view of the rotary osteotome of FIG. 10 but from a different point of view.
Figure 12:
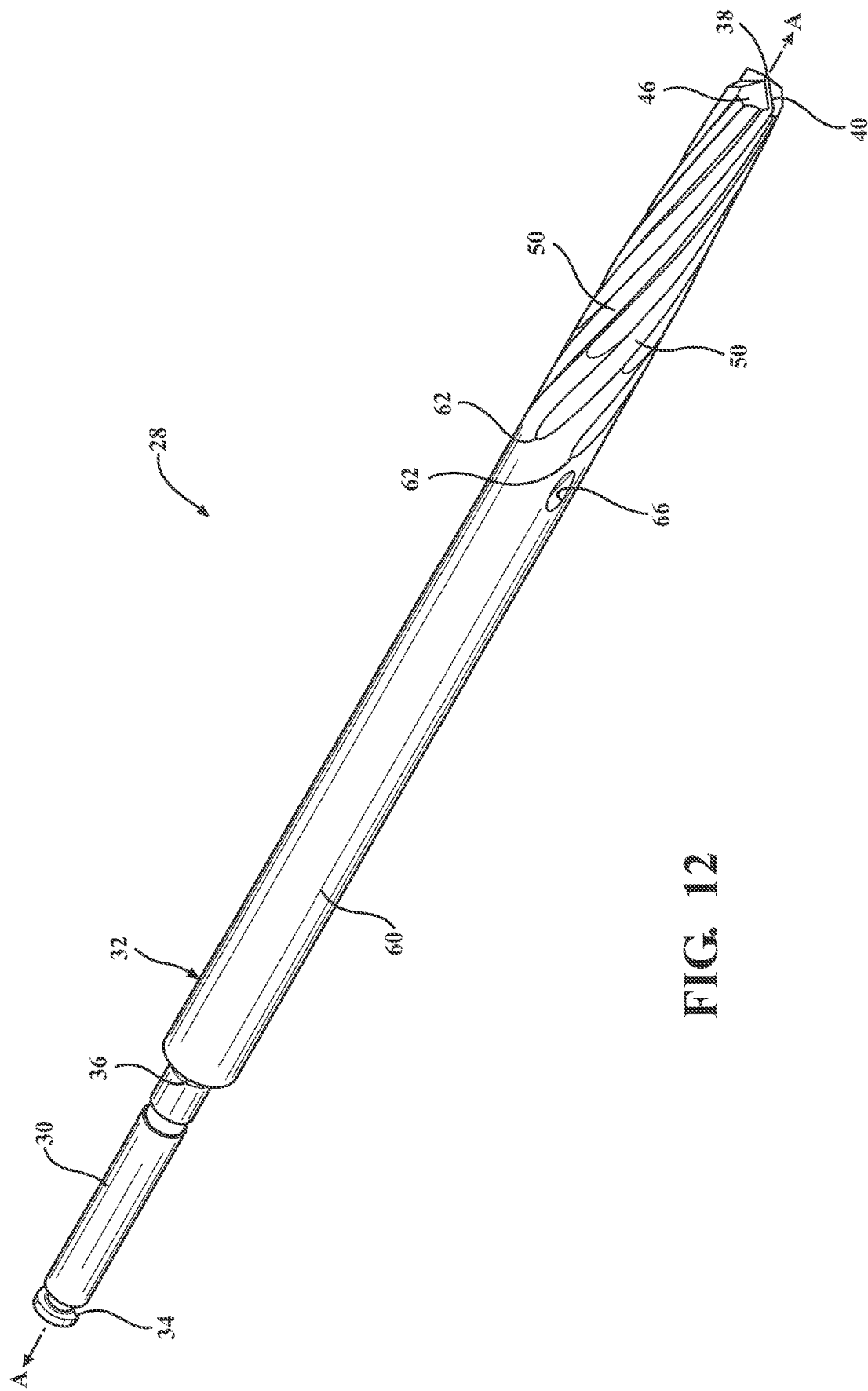
FIG. 12 is a perspective view of an extended length rotary osteotome according to an embodiment of the present invention.

The rotary osteotome 28 of this present invention is particularly configured for zygomatic and other deep reach applications. As such, the body 32 of the rotary osteotome 28 includes an elongated stopper section 60 that extends between the terminus 62 of the flutes 50 and the transition 36. The stopper section 60 produces a vital plugging action to prevent the continued migration of bone particles along the flutes 50 in cutting mode, and thereby self-arrest the cutting performance of the osteotome 28 when operated in the cutting direction. In practice, the axial length of the stopper section 60 can vary depending on the intended application. FIGS. 10 and 11 show rotary osteotomes 28 having relatively short stopper sections 60 intended for placing medium 22 and short 24 implants. By contrast, FIGS. 1B and 12 show rotary osteotomes 28 having relatively long stopper sections 60 intended for placing long implants 20.

In some contemplated embodiments, the entire length of the body 32, from apical end 38 to transition 36, has a continuous taper or conical profile. In these cases, the stopper section 60 will share this tapered configuration. However, in the illustrated examples the stopper section 60 has a straight cylindrical profile. Thus, only the lower end of the body 32 is tapered; a cylindrical shape occupies the stopper section 60, which is ideally suited to accommodate the shape of may zygomatic and other deep reach style implants 20, 22, 24.

Figure 13:
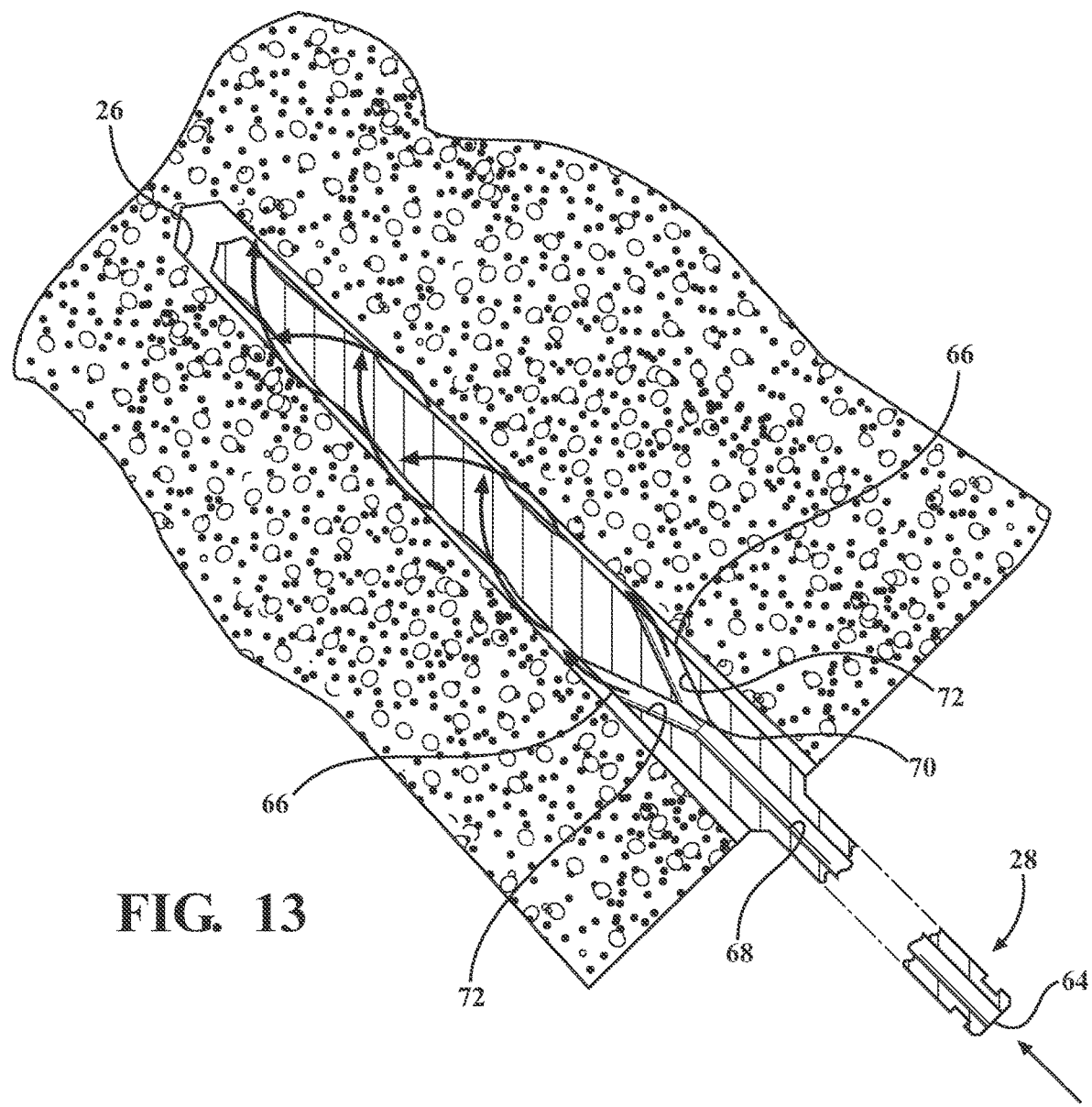
FIG. 13 a simplified cross-section through an osteotomy showing a rotary osteotome also in cross-section with irrigating fluid being discharged therefrom to generate beneficial hydrodynamic effects.

In reference to FIGS. 1B and 13, observe that once the entire lengths of the flutes 50 have entered the osteotomy 26, there is no convenient egress for the bone particle slurry from the flutes 50. The stopper section 60 seals or traps the bone particles between the flutes 50 and the sidewalls of the osteotomy 26 like a cork or piston. If the surgeon continues to advance the rotating osteotome 28 deeper into the osteotomy 26, substantial resistance will be encountered. The trapped bone chip slurry will become pressurized inside the flutes 50 in response to the force of the surgeon's push. Hydraulic pressure can be pulsated through the bone particle slurry, if the surgeon wishes, by the aforementioned pumping action which forces the slurry into the surrounding wall surfaces of the osteotomy 26, thereby forming a densification crust.

As perhaps best shown in FIG. 7, the rotary osteotome 28 includes an irrigation conduit passing from at least one inlet 64 in the shank 30 to at least one outlet orifice 66 in the body 32. The inlet 64 is disposed in the drive end of the shank 30, being aligned along the longitudinal axis A within the feature of the drive coupling 34. The irrigation conduit is defined by a generally cylindrical, i.e., tubular, main trunk 68 that extends through the shank 30, coincidentally along the longitudinal axis A, and also through a portion of the body 32. More specifically, the main trunk 68 passes through a significant portion of the stopper section 60, coincidentally along the longitudinal axis A. Due to the sometimes-high rotational velocities of the osteotome 28 in normal use (2000 RPM), the central disposition of the main trunk 68 has at least two important benefits: 1) rotational balance of the osteotome 28 is preserved; and 2) minimal transfer of motion via boundary layer friction to irrigation fluid transiting the main trunk 68.

As stated previously, it is contemplated that the irrigation conduit is provided with at least one outlet orifice 66. And the outlet orifice 66 is preferably disposed in the stopper section 60. However, to maintain rotational balance, a plurality of outlet orifices 66 are preferred. The plural outlet orifices 66 are spaced apart from one another in equal circumferential increments about the body 32. In the illustrated examples, the osteotome 28 is provided with two outlet orifices 66 diametrically opposed to one another. However, more than two outlet orifices 66 are certainly possible, provided the circumferential spacing maintains rotational balance. Naturally, one could envision an equivalent configuration of outlet orifices 66 arranged in clusters, where the clusters are equally circumferentially spaced apart even though individual orifices 66 may be unequally spaced.

The main objective is thus to maintain rotational stability and balance at speeds approaching 2000 RPM.

A flow splitter 70 is disposed between the main trunk 68 and the plurality of outlet orifices 66. The flow splitter 70 is configured to divide the flow of irrigating fluid traveling through the main trunk 68 into substantially equal branches 72 to be emitted through the respective the orifices 66. Each branch 72 is angled at an acute trajectory B relative to the longitudinal axis in the direction of the apical end, as best seen in FIG. 7. The acute trajectory B of each branch 72 is between about 10° and 45°. Preferably, the acute trajectory B is the same for all branches 72 to preserve rotational balance. However, those of skill in the art can envision ways to maintain rotational balance while making the acute trajectories B unequal among the branches 72. In the illustrated examples, the acute trajectory B of each branch is about 20°, which has been shown to provide satisfactory results.

Each outlet orifice 66 has a generally elliptical shape defined by a longer major axis and a shorter minor axis according to the normal rules of geometry. The major axis is oriented axially, whereas the minor axis is oriented circumferentially in the illustrated examples. The elliptical shape creates a specialized nozzle effect that is particularly adapted for zygomatic and deep reach applications. In particular, the elliptical shape of each orifice 66 has the effect of naturally bending the emitted streams of water into the waiting flutes 50. Surface tension along the boundary layer of the transiting liquid causes the irrigating fluid to cling to the inside surface of the branch 72. That means water exiting each orifice 66 will be urged by this natural effect to remain in contact with the body 32 and roll into the flutes 50.

To fully exploit this law of fluid mechanics, each outlet orifice 66 can be axially aligned with the terminus 62 of a respective flute 50, as shown throughout the illustrations. This alignment of orifices 66 and flutes 50 only improves the transfer of irrigating fluid into the flutes 50 where it can be pumped toward the apical end 38. Proximity of the orifice 66 to its associated flute terminus 62 naturally plays a role. In practice, it has been found that the distance from an orifice 66 to an adjacent flute terminus 62 should be no more than three lengths, regardless of alignment condition. That is to say, there should be no more than three times (3×) the major diameter of the elliptical shape in space between orifice and terminus 62 even if they are not axially aligned. Closer is generally considered better in this instance, such that a spacing less than a length (i.e., major diameter of orifice 66) coupled with axial alignment is considered optimal in many applications.

In practice, many zygomatic and other deep reach applications call for particularly narrow (slim) implants 20, 22, 24. That means the diameters of the rotary osteotomes 28 are likewise narrow/slim. The aforementioned hydraulic pumping effect that is enhanced by the flutes 50 is somewhat muted or frustrated when the diameter of the rotary osteotome 28 is narrow. (Larger diameters naturally generate larger angular velocities.) Therefore, even minor improvements in efficiency are welcomed.

FIG. 13 shows that when the outlet orifices 66 pass deep into the osteotomy 26, an energetic feed of irrigating fluid through the branches 72 is needed to maintain the desired hydraulic effect with its many preconditioning advantages, which include: 1) gentle pre-stressing of the bone structure of the osteotomy 26 in preparation for subsequent compacting contact, 2) haptic feedback transmitted through the rotary osteotome that allows the surgeon to tactically discern the instantaneously applied pressure prior to actual contact between the rotary osteotome and side walls, 3) enhanced hydration of the bone structure which increases bone toughness and increases bone plasticity, 4) hydraulically assisted infusion of bone fragments into the lattice structure of the surrounding bone, 5) reduced heat transfer especially at the point of plastic deformation, 6) hydrodynamic lubricity, and 7) dampening or cushioning of the trauma sensed by the patient, to name a few.

Figure 14:
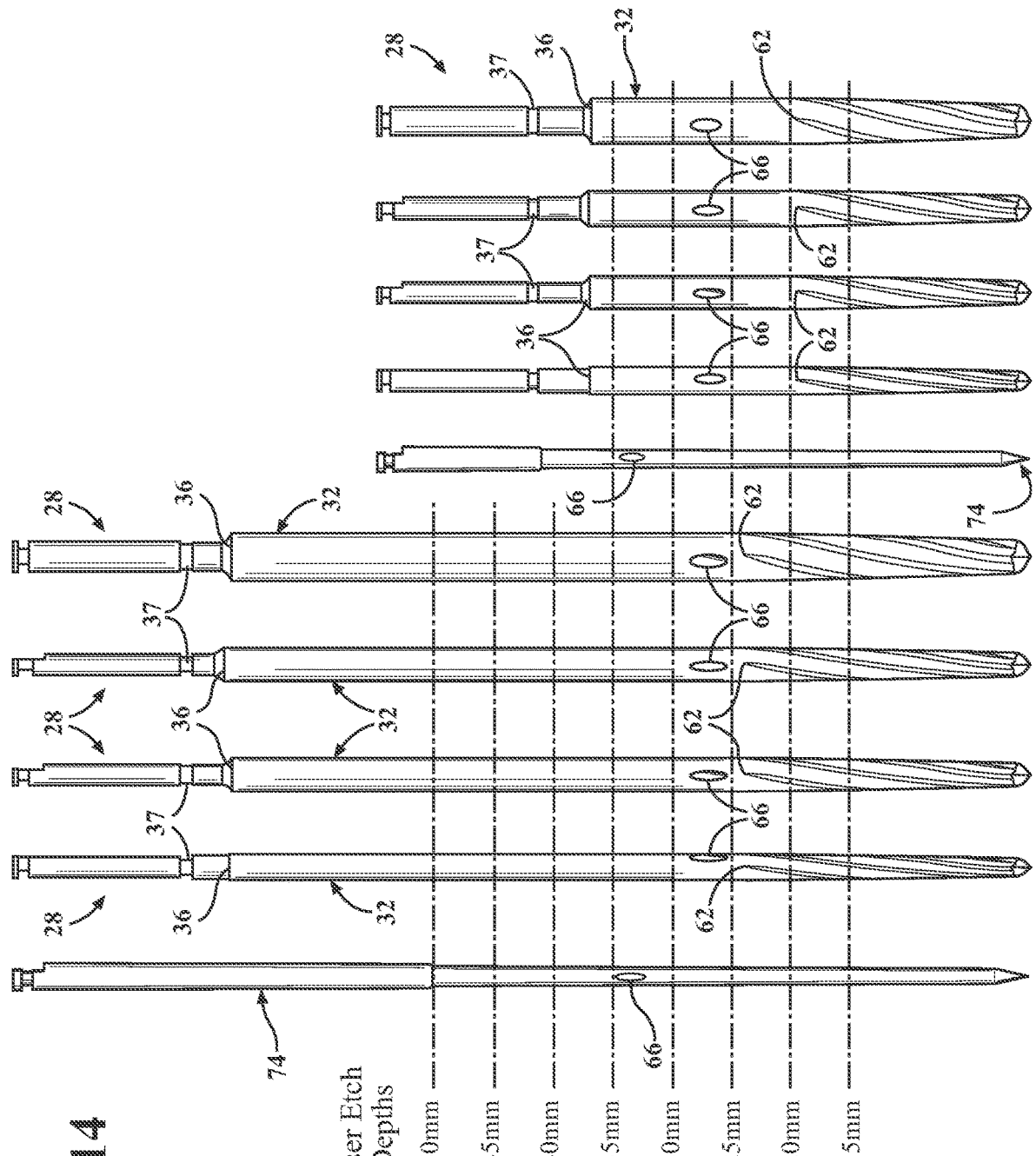
FIG. 14 shows side-by-side comparisons of several different diameter and different length osteotomes incorporating the novel irrigation duct of this invention.

FIG. 14 provides side-by-side comparisons for two sets of rotary osteotomes 28. Each set is composed of a pilot drill 74 and four rotary osteotomes 28 of the same length but progressively larger diameters. The set on the left are formed with extended lengths to enable placement of long implants 20. Although presumably these extended length osteotomes 28 could be used to place the other implants 22, 24 as well. The set on the right are formed with shorter lengths to enable placement of medium 22 and short 24 implants only.

Figure 15:
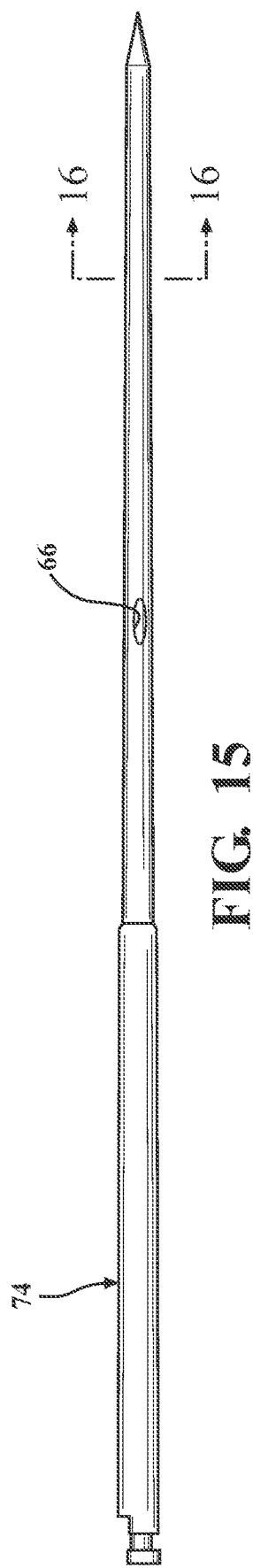
FIG. 15 shows the novel irrigation duct of this invention incorporated into a pilot drill having a triangular cross-section.
Figure 16:
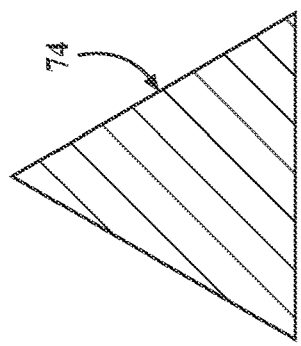
FIG. 16 is a cross-section taken generally along lines 16-16 in FIG. 15.

The pilot drill 74 can be of any suitable type. The version shown in FIGS. 14-16 is a lance style having a triangular cross-section. This style has been found to provide satisfactory results. As can be appreciated from the inclusion of outlet orifices 66, the pilot drill 74 may also be configured for internal irrigation using a similar irrigation conduit scheme to that described above in connection with the rotary osteotomes 28.

Methods of use have been well-documented, at least in the context of externally irrigated osteotomes. Detailed descriptions for methods of use may be had, for example, in WO 2017/124079 A1 published 20 Jul. 2017. In jurisdictions that permit incorporation by reference, the entire disclosure of WO 2017/124079 A1 is hereby incorporated by reference.

The principles of this invention are not limited to bone as the host material. Indeed, the osteotome 28 of this invention may be configured to enlarge a hole in almost any type of cellular or solid material by cutting and/or compacting. (In non-medical applications, the rotary osteotome 28 should be identified as simply a tool or rotary tool to avoid confusion with the osteo-prefix which implies use in bone.) Metal foam of the type used in aerospace, heat shielding and other critical applications is a viable host material candidate. The hole formed by the rotary tool 28 of this invention is better prepared to receive a screw or other fixation anchor because its inner sidewall has been densified by the aforementioned compressive displacement and auto-grafting effects. In addition to foam metals, any inorganic materials that have visco-elastic properties similar to live bone are especially good candidates. Some experimentation has been made as well with hole formation in non-cellular inorganic materials like plate aluminum and plastic. Certain benefits have presented as well in these non-cellular materials, such that the potential to improve screw or anchor retention by hole preparation using the principles of this invention are fully contemplated.

Those of skill in the art will appreciate that the osteotome 28 could be configured with a fully straight or non-tapered body 32 rather than the partially tapered working end as shown in the illustrations. Accordingly, the described osteotomy enlargement techniques can be accomplished using non-tapered tools via the novel method of compacting in combination with hydrodynamic effects. Thus, the foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A rotary osteotome configured for deep reach applications, said rotary osteotome comprising:
    a shank establishing a longitudinal axis of rotation, said shank extending between a drive end and a transition interface,
    a body extending from said transition interface to an apical end, a portion of said body comprising a fluted tip, said fluted tip having a maximum diameter, a plurality of flutes disposed about said fluted tip and extending from adjacent said apical end to respective terminus, each said flute having a cutting face on one side thereof defining a rake angle and a densifying face on the other side thereof defining a heel-side angle, a land formed between each adjacent pair of flutes, each said land having a working edge along said cutting face of the one adjacent said flute, a portion of said body adjacent said fluted tip comprising a stopper section, said stopper section disposed between said terminus of said flutes and said transition interface of said shank, said stopper section comprising a cylindrically straight or tapered portion of said body having a diameter equal to or greater than said maximum diameter of said fluted tip,
    an irrigation conduit passing from at least one inlet in said shank to a plurality of outlet orifices, said plurality outlet orifices disposed in said stopper section,
    wherein said plurality of outlet orifices are spaced apart from one another in equal circumferential increments about said body, and
    wherein each said outlet orifice has a generally elliptical shape defined by a longer major axis and a shorter minor axis, each said outlet orifice being located with respect to an adjacent said flute by spacing not more than three times the length of said major axis.

2. The rotary osteotome of claim 1 wherein said plurality of outlet orifices comprise two diametrically opposed outlet orifices.

3. The rotary osteotome of claim 1 each said outlet orifice is axially aligned with said terminus of a respective said flute.

4. The rotary osteotome of claim 1 said irrigation conduit includes a generally cylindrical main trunk extending through said shank coincidentally along said longitudinal axis, said main trunk extending through a portion of said stopper section coincidentally along said longitudinal axis, said irrigation conduit further including a flow splitter disposed between said main trunk and said plurality of outlet orifices.

5. The rotary osteotome of claim 4 wherein said flow splitter is configured to divide the flow of irrigating fluid through said main trunk into substantially equal branches to be emitted through the respective said orifices, each said branch being angled at an acute trajectory relative to said longitudinal axis in the direction of said apical end.

6. The rotary osteotome of claim 5 wherein said acute trajectory of each said branch is between about 10° and 45°.

7. A rotary osteotome configured for deep reach applications, said rotary osteotome comprising:
    a shank establishing a longitudinal axis of rotation, said shank extending between a drive end and a transition interface,
    a body extending from said transition interface to an apical end, at least a portion of said body comprising a fluted tip, said fluted tip having a conically tapered profile decreasing from a maximum diameter to a minimum diameter adjacent said apical end, a plurality of flutes disposed about said body and extending from adjacent said apical end to respective terminus, each said flute helically spiraling about said conically tapered profile of said fluted tip, said plurality of flutes arranged about said body in equal circumferential increments, each said flute having a cutting face on one side thereof defining a rake angle and a densifying face on the other side thereof defining a heel-side angle, a land formed between each adjacent pair of flutes, each said land having a working edge along said cutting face of the one adjacent said flute, a portion of said body adjacent said fluted tip comprising a stopper section, said stopper section disposed between said terminus of said flutes and said transition interface of said shank, said stopper section being generally cylindrical or tapered and having a diameter equal to or greater than said maximum diameter of said fluted tip, an irrigation conduit passing from an inlet in said shank to a plurality of outlet orifices disposed in said stopper section, said inlet disposed in said drive end of said shank, said inlet being aligned along said longitudinal axis, said plurality of outlet orifices spaced apart from one another in equal circumferential increments about said body, and wherein each said outlet orifice has a generally elliptical shape defined by a longer major axis and a shorter minor axis, each said outlet orifice being located with respect to an adjacent said flute by a spacing not more than three times the length of said major axis.

8. The rotary osteotome of claim 7 wherein said plurality of outlet orifices comprise two diametrically opposed outlet orifices.

9. The rotary osteotome of claim 7 wherein each said outlet orifice is axially aligned with said terminus of a respective said flute.

10. The rotary osteotome of claim 7 wherein said irrigation conduit includes a generally cylindrical main trunk extending through said shank coincidentally along said longitudinal axis, said main trunk extending through a portion of said stopper section coincidentally along said longitudinal axis, said irrigation conduit further including a flow splitter disposed between said main trunk and said plurality of outlet orifices.

11. The rotary osteotome of claim 10 wherein said flow splitter is configured to divide the flow of irrigating fluid through said main trunk into substantially equal branches to be emitted through the respective said orifices, each said branch being angled at an acute trajectory relative to said longitudinal axis in the direction of said apical end.

12. The rotary osteotome of claim 11 wherein said acute trajectory of each said branch is between about 10° and 45°.

13. The rotary osteotome of claim 7 wherein each said working edge is substantially margin-less, said working edges winding about said body in a direction that turns away from a non-cutting direction as said conically tapered profile decreases in diameter, said apical end including a pair of lips, each said lip having a generally planar first trailing flank.

* * * * *